US009624498B2

(12) United States Patent
Froelich et al.

(10) Patent No.: US 9,624,498 B2
(45) Date of Patent: Apr. 18, 2017

(54) METHODS AND COMPOSITIONS FOR REGULATION OF ZINC FINGER PROTEIN EXPRESSION

(71) Applicant: Sangamo BioSciences, Inc., Richmond, CA (US)

(72) Inventors: Steven Froelich, Richmond, CA (US); Philip D. Gregory, Richmond, CA (US); H. Steve Zhang, Richmond, CA (US)

(73) Assignee: SANGAMO BIOSCIENCES, INC., Richmond, CA (US)

( * ) Notice: Subject to any disclaimer, the term of this patent is extended or adjusted under 35 U.S.C. 154(b) by 0 days.

(21) Appl. No.: 14/661,763

(22) Filed: Mar. 18, 2015

(65) Prior Publication Data

US 2015/0267205 A1 Sep. 24, 2015

Related U.S. Application Data

(60) Provisional application No. 61/955,002, filed on Mar. 18, 2014.

(51) Int. Cl.
*C12N 15/63* (2006.01)
*C12N 15/86* (2006.01)

(52) U.S. Cl.
CPC ............. *C12N 15/63* (2013.01); *C12N 15/86* (2013.01); *C12N 2830/60* (2013.01)

(58) Field of Classification Search
None
See application file for complete search history.

(56) References Cited

U.S. PATENT DOCUMENTS

| | | | |
|---|---|---|---|
| 5,789,538 A | 8/1998 | Rebar et al. |
| 5,925,523 A | 7/1999 | Dove et al. |
| 5,928,638 A | 7/1999 | Uchida et al. |
| 6,007,988 A | 12/1999 | Choo |
| 6,013,453 A | 1/2000 | Choo |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,358,085 B2 | 4/2008 | Zhang et al. |
| 7,361,635 B2 | 4/2008 | Miller et al. |
| 7,534,775 B2 | 5/2009 | Zhang et al. |
| 7,837,668 B2 | 11/2010 | Gasmi et al. |
| 7,888,121 B2 | 2/2011 | Urnov et al. |
| 7,914,796 B2 | 3/2011 | Miller et al. |
| 7,947,873 B2 | 5/2011 | Li et al. |
| 7,951,925 B2 | 5/2011 | Ando et al. |
| 7,972,843 B2 | 7/2011 | Hoffman |
| 7,972,854 B2 | 7/2011 | Miller et al. |
| 8,034,598 B2 | 10/2011 | Miller |
| 8,092,429 B2 | 1/2012 | Gasmi et al. |
| 8,110,379 B2 | 2/2012 | DeKelver et al. |
| 8,409,861 B2 | 4/2013 | Guschin et al. |
| 8,586,526 B2 | 11/2013 | Gregory et al. |
| 8,623,618 B2 | 1/2014 | Doyon et al. |
| 8,703,489 B2 | 4/2014 | Wang |
| 8,772,453 B2 | 7/2014 | Paschon et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Bathe et al.; The transcription factor Snail is a repressor of E-cadherin gene expression in epithelial tumour cells; Nature Cell Biology; vol. 2; pp. 84-89; Feb. 2000.*
Miller et al.; A TALE nuclease architecture for efficient genome editing; Nature Biotechnology; vol. 29; No. 2; pp, 143-148; Feb. 2011.*
Stratagene; Gene Characterization Kits; 1998 Catalog, p. 39.*
Zhang et al.; Efficient construction of sequence-specific TAL effectors for modulating mammalian transcription; Nature Biotechnology; vol. 29; No. 2, Feb. 2011, pp. 149-154.*

(Continued)

*Primary Examiner* — Antonio Galisteo Gonzalez

(74) *Attorney, Agent, or Firm* — Pasternak Patent Law; Susan Abrahamson

(57) ABSTRACT

The present disclosure is in the field of genome engineering, particularly regulating targeted modification of the genome.

22 Claims, 12 Drawing Sheets

(56) References Cited

U.S. PATENT DOCUMENTS

| | | |
|---|---|---|
| 2006/0239966 A1 | 10/2006 | Tornøe et al. |
| 2007/0134796 A1 | 6/2007 | Homes et al. |
| 2007/0218528 A1 | 9/2007 | Miller |
| 2008/0159996 A1 | 7/2008 | Ando et al. |
| 2008/0188000 A1 | 8/2008 | Reik et al. |
| 2009/0117617 A1 | 5/2009 | Homes et al. |
| 2009/0136465 A1 | 5/2009 | Merenick et al. |
| 2009/0305419 A1 | 12/2009 | Miller |
| 2010/0003756 A1 | 1/2010 | Collingwood et al. |
| 2010/0218264 A1 | 8/2010 | Cui et al. |
| 2011/0082078 A1 | 4/2011 | Dent et al. |
| 2011/0082093 A1 | 4/2011 | Gregory et al. |
| 2011/0201055 A1 | 8/2011 | Doyon et al. |
| 2011/0207221 A1 | 8/2011 | Cost et al. |
| 2011/0265198 A1 | 10/2011 | Gregory et al. |
| 2011/0281361 A1 | 11/2011 | DeKelver et al. |
| 2012/0017290 A1 | 1/2012 | Cui et al. |
| 2012/0040398 A1 | 2/2012 | Miller |
| 2012/0128635 A1 | 5/2012 | Gregory et al. |
| 2012/0196370 A1 | 8/2012 | Urnov et al. |
| 2012/0214241 A1 | 8/2012 | Laganiere et al. |
| 2013/0122591 A1 | 5/2013 | Cost et al. |
| 2013/0137104 A1 | 5/2013 | Cost et al. |
| 2013/0145484 A1 | 6/2013 | Logtenberg et al. |
| 2013/0177960 A1 | 7/2013 | Rebar |
| 2013/0177983 A1 | 7/2013 | Rebar |
| 2013/0253040 A1 | 9/2013 | Miller et al. |
| 2014/0017212 A1 | 1/2014 | Rebar |
| 2014/0080216 A1 | 3/2014 | Cost et al. |
| 2014/0093913 A1 | 4/2014 | Cost et al. |
| 2015/0056705 A1 | 2/2015 | Conway et al. |
| 2015/0064789 A1 | 3/2015 | Paschon et al. |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/099084 A2 | 12/2002 |
| WO | WO 03/016496 A2 | 2/2003 |
| WO | WO 2010/079430 A1 | 7/2010 |

OTHER PUBLICATIONS

Alvarez, et al., "A Phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients," *Hum. Gene Ther.* 8(5):597-613 (1997).

Beerli, et al., "Engineering Polydactyl Zinc-Finger Transcription Factors," *Nature Biotechnol.* 20:135-141(2002).

Beerli, et al., "Positive and Negative Regulation of Endogenous Genes by Designed Transcription Factors," *PNAS USA* 97(4):1495-1500 (2000).

Beurdeley, et al., "Compact Designer Talens for Efficient Genome Engineering," *Nature Communications* 4:1762 (2013) doi:10.10.38/ncomms2782.

Blaese, et al., "T Lymphocyte-Directed Gene Therapy for ADA-SCID: Initial Trial Results After 4 Years," *Science* 270(5235):475-480 (1995).

Boch, et al., "Breaking the Code of DNA Binding Specificity of TAL-Type III Effectors," *Science* 326:1509-1512 (2009).

Boissel, et al., "Megatals: A Rare-Cleaving Nuclease Architecture for Therapeutic Genome Engineering," *Nucl. Acid Res.* 1-13 (2013) doi: 10.1093/nar/gkt1224.

Bonas, et al., "Genetic and Structural Characterization of the Avirulence Gene AVRBS3 From *Xanthomonas campestris* pv. *vesicatoria*" *Mol. Gen. Genet.* 218:127-136 (1989).

Choo, et al., "Advances in Zinc Finger Engineering," *Curr. Opin. Struct. Biol.* 10:411-416 (2000).

Christian, et al., "TAL Effector Nucleases Create Targeted DNA Double-Strand Breaks," *Genetics* epub 10.1534/genetics.110.120717.

Dranoff, et al., "A Phase I Study of Vaccination With Autologous, Irradiated Melanoma Cells Engineered to Secrete Human Granulocyte-Macrophage Colony Stimulating Factor," *Hum. Gene Ther.* 8(1):111-123 (1997).

Dull, et al., "A Third-Generation Lentivirus Vector With a Conditional Packaging System," *J. Virol.* 72:8463-8471 (1998).

Dunbar, et al., "Retrovirally Marked CD34-Enriched Peripheral Blood and Bone Marrow Cells Contribute to Long-Term Engraftment After Autologous Transplantation," *Blood* 85:3048-3057 (1995).

Ellem, et al., "A Case Report: Immune Responses and Clinical Course of the First Human Use of Granulocyte/Macrophage-Colony-Stimulating-Factor-Transduced Autologous Melanoma Cells for Immunotherapy," *Cancer Immunol. Immunother.* 44(1):10-20(1997).

Follenzi, et al., Gene Transfer by Lentiviral Vectors Is Limited by Nuclear Translocation and Recued by HIV-I POL Sequences, *Nature Genetics* 25:217-222 (2000).

Hermonat & Muzyczka, "Use of Adeno-Associated Virus as a Mammalian DNA Cloning Vector: Transduction of Neomycin Resistance Into Mammalian Tissue Culture Cells," *PNAS USA* 81(20):6466-6470 (1984).

Heuer, et al., "Repeat Domain Diversity of AVRBS3-Like Genes in Ralstonia Solanacearum Strains and Association With Host Preferences in the Field," *Appl. and Envir. Micro.* 73(13):4379-4384 (2007).

Isalan, et al., "A Rapid, Generally Applicable Method to Engineer Zinc Fingers Illustrated by Targeting the HIV-1 Promoter," *Nat. Biotechnol.* 19:656-660 (2001).

Jinek, et al., "RNA-Programmed Genome Editing in Human Cells," *eLife* 2:e00471 (2013).

Jinek, et al., "A Programmable Dual-RNA-Guided DNA Endonuclease in Adaptive Bacterial Immunity," *Science* 337:816-821 (2012).

Kay, et al., "A Bacterial Effector Acts as a Plant Transcription Factor and Induces a Cell Size Regulator," *Science* 318:648-651 (2007).

Kearns, et al., "Recombinant Adeno-Associated Virus (AAV-CFTR) Vectors Do Not Integrate in a Site-Specific Fashion in an Immortalized Epithelial Cell Line," *Gene Ther.* 3(9):748-755 (1996).

Kim, et al., "Hybrid Restriction Enzymes: Zinc Finger Fusions to FOK I Cleavage Domain," *PNAS USA* 93(3):1156-1160 (1996).

Kohn, et al., "Engraftment of Gene-Modified Umbilical Cord Blood Cells in Neonates With Adenosine Deaminase Deficieny," *Nat. Med.* 1:1017-1023 (1995).

Lois, et al., "Germline Transmission and Tissue-Specific Expression of Transgenes Delivered by Lentiviral Vectors," *Science* 295(5556):868-872 (2002).

Malech, et al., "Prolonged Production of NADPH Oxidase-Corrected Granulocytes After Gene Therapy of Chronic Granulomatous Disease," *PNAS USA* 94(22):12133-12138 (1997).

Moscou, et al., "A Simple Cipher Governs DNA Recognition by TAL Effectors," *Science* 326:1501 (2009).

Nagai, et al., "A Variant of Yellow Fluorescent Protein With Fast and Efficient Maturation for Cell-Biological Applications," *Nature Biotech.* 20(1):87-90 (2002).

Naldini, et al., "Efficient Transfer, Integration, and Sustained Long-Term Expression of the Transgene in Adult Rat Brains Injected With a Lentiviral Vector," *Proc. Natl. Acad. Sci. USA* 93:11382-11388 (1996).

Pabo, et al., "Design and Selection of Novel CYS2HIS2 Zinc Finger Proteins," *Ann. Rev. Biochem.* 70:313-340 (2001).

Peiro, et al., "SNAIL1 Transcriptional Repressor Binds to Its Own Promoter and Controls Its Expression," *Nucleic Acids Research* 34(7):2077-2084 (2006).

(56) References Cited

OTHER PUBLICATIONS

Perez-Pinera, et al., "RNA-Guided Gene Activation by CRISPR-CAS9-Based Transcription Factors," *Nature Methods* 10:973-976 (2013).

Rosenecker, et al., "Adenovirus Infection in Cystic Fibrosis Patients: Implications for the Use of Adenoviral Vectors for Gene Transfer," *Infection* 24:5-10 (1996).

Samulski, et al., "Helper-Free Stocks of Recombinant Adeno-Associated Viruses: Normal Integration Does Not Require Viral Gene Expression," *J. Virol.* 63:03822-3828 (1989).

Schornack, et al., "Gene-For-Gene-Mediated Recognition of Nuclear-Targeted AVRBS3-Like Bacterial Effector Proteins," *J. Plant Physiol.* 163(3):256-272 (2006).

Segal, et al., "Custom DNA-Binding Proteins Come of Age: Polydactyl Zinc-Finger Proteins," *Curr. Opin. Biotechnol.* 12:632-637 (2001).

Segal, et al., "Bacteria Herald a New Era of Gene Editing," *eLife* 2:e00653 (2013).

Sheng, et al., "Structure-Based Cleavage Mechanism of Thermus Thermophilus Argonaute DNA Guide Strand-Mediated DNA Target Cleavage," *Proc. Natl. Acad. Sci. USA* 111(2):652-657 (2013) doi: 10.1073/pnas.1321032111.

Sterman, et al., "Adenovirus-Mediated Herpes Simplex Virus Thymidine Kinase/ Ganciclovir Gene Therapy in Patients With Localized Malignancy: Results of a Phase 1 Clinical Trial in Malignant Mesothelioma," *Hum. Gene Ther.* 7:1083-1089 (1998).

Swarts, et al., "DNA-Guided DNA Interference by a Prokaryotic Argonaute," *Nature* 507(7491):258-261 (2014).

Tebas, et al., "Gene Editing of CCR5 in Autologous CD4 T Cells of Persons Infected With HIV," *New Eng. J. Med.* 370(10):901 (2014).

Topf, et al., "Regional 'Pro-Drug' Gene Therapy: Intravenous Administration of an Adenoviral Vector Expressing the *E. coli* Cytosine Deaminase Gene and Systemic Administration of 5-Fluorocytosine Suppresses Growth of Hepatic Metastasis of Colon Carcinoma," *Gene Ther.* 5:507-513 (1998).

Tratschin, et al., "A Human Parvovirus, Adeno-Associated Virus, as a Eucaryotic Vector: Transient Expression and Encapsidation of the Procaryotic Gene for Chloramphenicol Acetyltransferase," *Mol. Cell. Biol.* 4:2072-2081 (1984).

Wagner, et al., "Efficient and Persistent Gene Transfer of AAV-CFTR in Maxillary Sinus," *Lancet* 321(9117):1702-1703 (1998).

Welsh, et al., "Adenovirus-Mediated Gene Transfer for Cystic Fibrosis: Part A. Safety of Dose and Repeat Administration in the Nasal Epithelium. Part B. Clinical Efficacy in the Maxillary Sinus," *Hum. Gene Ther.* 2:205-218 (1995).

Yu, et al., "An Engineered VEGF-Activating Zinc Finger Protein Transcription Factor Improves Blood Flow and Limb Salvage in Advanced-Age Mice," *FASEB J.* 20:479-481 (2006).

Zufferey, et al., "Self-Inactivating Lentivirus Vector for Safe and Efficient In Vivo Gene Delivery," *J. Virol.* 72:9873-9880 (1998).

\* cited by examiner

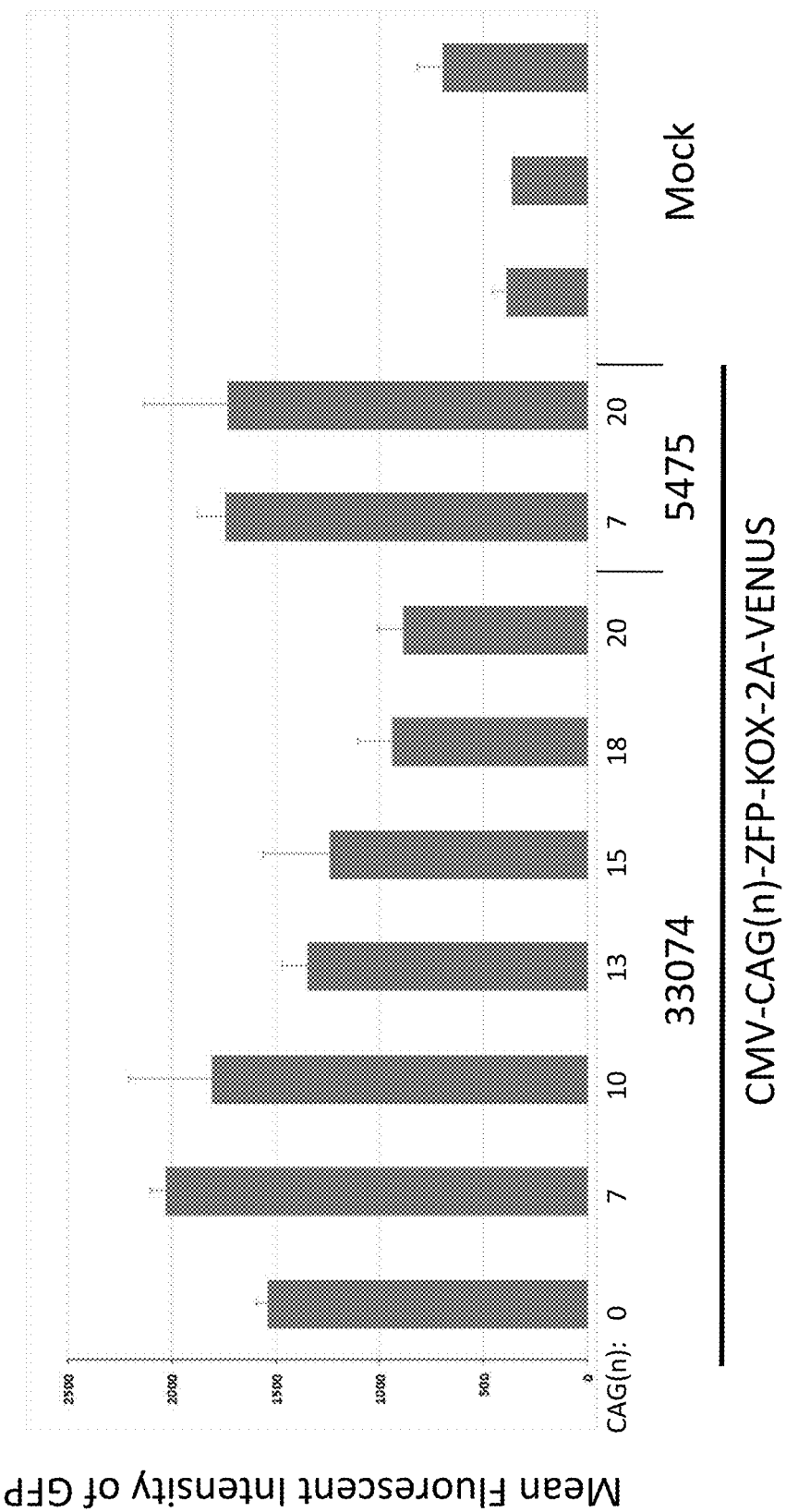

METHODS AND COMPOSITIONS FOR REGULATION OF ZINC FINGER PROTEIN EXPRESSION

CROSS-REFERENCE TO RELATED APPLICATIONS

The present application claims the benefit of U.S. Provisional Application No. 61/955,002, filed Mar. 18, 2014, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 19, 2015, is named 8325-0113_SL.txt and is 7,290 bytes in size.

TECHNICAL FIELD

The present disclosure is in the field of genome expression and engineering, particularly in the regulation of the expression of gene modulators such as transcription factors and nucleases in a cell.

BACKGROUND

Various methods and compositions for targeted modulation of gene expression of endogenous genomic DNA have been described. Targeted modulation of gene expression by DNA-binding proteins is described, for example, in U.S. Pat. Nos. 6,534,261; 6,607,882; 6,599,692; 6,689,558; 7,067,317; 7,947,873; 7,253,273; 7,358,085; 7,361,635; 7,534,775; 8,586,526 and U.S. Patent Publication No. 20110082093. Furthermore, targeted cleavage events using site-specific nucleases can be used, for example, to induce targeted mutagenesis, induce targeted deletions of cellular DNA sequences, and facilitate targeted recombination at a predetermined chromosomal locus. See, for example, U.S. Pat. Nos. 8,623,618; 8,034,598; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20060063231; 20080159996; 201000218264; 20120017290; 20110265198; 20130137104; 20130122591; 20130177983 and 20130177960 and U.S. application Ser. No. 14/278,903, the disclosures of which are incorporated by reference in their entireties for all purposes.

These methods often involve the use of engineered proteins that modulate expression of a target gene or engineered nuclease systems. In particular, the engineered transcription factors activate or repress targeted genes and the nucleases induce a double strand break (DSB) or a nick in a target DNA sequence such that repair of the break by non-homologous end joining (NHEJ) or homology directed repair (HDR) can result in the knock out of a gene and/or the insertion of a sequence of interest (targeted integration). Modulation and/or cleavage of endogenous genes can occur through the use of proteins and systems such as zinc finger protein transcription factors (ZFP-TFs), zinc finger nucleases (ZFNs), transcription-activator like effector transcription factors (TALE-TFs), CRISPR/Cas transcription factors (see, e.g., Perez-Pinera et al. (2013) *Nature Methods* 10:973-976), transcription-activator like effector nucleases (TAL-ENs), Ttago nucleases or using the CRISPR/Cas system with an engineered crRNA/tracr RNA ('single guide RNA') to guide specific cleavage. Clinical trials using these engineered transcription factors containing zinc finger proteins have shown that these novel transcription factors are capable of treating various conditions (see, e.g., Yu et al. (2006) *FASEB J.* 20:479-481). Additionally, clinical trials using engineered zinc finger nucleases have also demonstrated therapeutic utility (see, e.g. Tebas et at (2014) *New Eng J Med* 370(10):901).

Gene modulation using these proteins and systems has the potential to treat various diseases and disorders, including, by way of example, HIV infection, cystic fibrosis, cancers such as glioblastomas, neuropathies, trinucleotide repeat disorders, HLA-related disorders, hemophilias, neurological conditions, pathogen infection, lysosomal storage diseases and hemoglobinopathies. See, e.g., U.S. Pat. No. 7,951,925; U.S. Patent Publication Nos. 20140017212; 20140093913; 20140080216; 20130145484, 20080188000, 20110082078, 20110082093, 20120196370, 20120128635, 20120214241, 20130253040. However, even in instances where the modulator preferentially binds (in a sequence-specific manner) to a target site mutant allele as compared to a wild-type allele (see, e.g., U.S. Patent Publication Nos. 20110082093 and 20130253040), over-expression of the modulator may result in binding to and/or undesired alteration of a wild-type sequence.

Thus, there remains a need for compositions and methods for regulating expression of exogenous gene-modulators within a cell to achieve optimal levels of expression of the modulators and subsequent modification of gene expression levels.

SUMMARY

The present invention describes compositions and methods for use in gene therapy, gene expression and genome engineering. Specifically, the methods and compositions described relate to regulation, including self-regulation, of a modulator of gene expression (e.g., molecules comprising one or more zinc finger proteins, TALEs, CRISPR/Cas components, etc. that increase or decrease gene expression) within a cell where the gene to be modulated can be an endogenous gene or can be in an expression cassette within the cell driving the expression of a transgene of interest.

In one aspect, the invention comprises a construct comprising a polynucleotide encoding at least one component of a gene modulator (e.g., transcription factor or nuclease, such as a ZFP-TF, ZFN, TALE-TF, TALEN, Ttago nuclease, or protein component of a CRISPR/Cas nuclease or transcription factor) and a sequence (e.g., promoter) wherein the polynucleotide also includes one or more low-affinity (self-regulating) target sequences that can be bound by the gene modulator. In certain embodiments, the sequence encoding the transcription factor or nuclease (or component thereof) is operably linked to the sequence including the one or more low-affinity (self-regulating) target sequences that can be bound by the gene regulator. In this way, expression of the gene modulator (e.g., transcription factor or nuclease) is self-regulating in that binding of the gene modulator to the low-affinity target sequence in the exogenous construct modulates (e.g., increases or decreases) expression of the gene modulator. Any number of low-affinity target sequences or portions of target sequences may be included in the constructs, for example, between 1 and 30 (or any number there-between). In certain embodiments, 1, 2, 3, 4, 5, 6, 7, 8, 9, 10, 11, 12, 13, 14, 15, 16, 17, 18, 19, or 20 low-affinity target sequences or portions thereof are included in the construct encoding the transcription factor or nuclease. The number of low-affinity target sequences or portions thereof may be based, for example, on the binding affinity of the zinc finger protein, with zinc finger proteins with high affinity for their target site typically linked to sequences with fewer low-affinity target sites than zinc finger proteins having lower affinity for their target sites. In certain embodiments, the intended target site is in an endogenous genome. The low-affinity target site may be the same or different than the intended target site. In certain embodiments, the low-affinity target site comprises the intended target site and additional intended target sites, additional target subsites (e.g., 3 base pairs for zinc finger proteins) or additional base pairs. In certain embodiments, the low-affinity (self-regulating) target site includes a different number of target sites or subsites, for example 1, 2, 3, 4, 5, 6, 7, 8, 9, 10 or even more additional or fewer target sites or target subsites (e.g., a low-affinity target site may be made up of 15-20 CAG repeats(SEQ ID NO: 20)as compared to 6 or 7 CAG repeats(SEQ ID NO: 21)in the intended target site). In certain embodiments, the low-affinity target sequence comprises a plurality of repeats (e.g., CAG and/or CCG repeats) and are included in the control element(s) driving expression of a transcription factor or nuclease that targets a gene involved in a trinucleotide repeat disorder (e.g., an Htt gene, see United States Patent Publication 20110082093). The sequence including the low affinity target sites may be located within and/or proximal to a promoter sequence or any other sequence in the expression construct (e.g., an enhancer sequence) provided that when the sequence is not bound by the transcription factor or nuclease, transcription is not largely affected by the presence of the sequence, but when bound, transcription is modulated (increased or decreased and/or shut off). In certain embodiments, the constructs as described herein further comprise a donor nucleic acid (or transgene).

In some embodiments, expression of a transgene of interest may also be also modulated by creating a fusion transgene such that the fusion transgene encodes both a gene modulator and a gene of interest. In some cases, the gene modulator and the gene of interest are separated by a self-cleaving peptide sequence (e.g. 2A) or a ribosomal pause site (e.g. IRES). In further embodiments, the gene of interest encodes a reporter gene.

In certain embodiments, the construct comprising the polynucleotides as described herein is a viral construct, for example a lentiviral vector (LV), an integration defective lentiviral vector (IDLV), an adenovirus or an AAV construct. In some embodiments, the gene modulator encoded by the construct comprises a transcription factor (e.g., a DNA-binding domain such as a zinc finger or TALE or a single guide RNA and a transcriptional regulatory domain such as an activation domain (e.g., modified Cas9 transactivator for a CRISPR/Cas system or a HSV VP16 domain for use with a ZFP or TALE system) or a repression domain (e.g. a KRAB domain)). In other embodiments, the construct encodes a nuclease, for example a DNA-binding protein (zinc finger protein or TALE) and a nuclease domain (e.g., cleavage domain) or a CRISPR/Cas nuclease. In certain embodiments, the gene modulator (e.g., transcription factor and/or nuclease) binds to a wild-type allele. Thus, the gene modulator may increase or decrease gene expression upon binding to a target site. In other embodiments, the gene modulator binds to a mutant allele. In still other embodiments, the gene modulator binds to both wild-type and mutant alleles (bi-allelic). The nuclease can induce a double-stranded (DSB) or single-stranded break (nick) in the target DNA. In some embodiments, two nickases are used to create a DSB by introducing two nicks. In some cases, the nickase is a ZFN, while in other cases, the nickase is a TALEN or a CRISPR/Cas nickase.

In other aspects, described herein are cells comprising one or more of the constructs described herein. In certain embodiments, the cells further comprise a donor nucleic acid (e.g., transgene), which may be included on the construct or provided separately (e.g., in a separate construct). Thus, the donor may be delivered prior to, after, or along with the nucleic acid encoding the nuclease(s). The donor nucleic acid comprises an exogenous sequence (transgene) to be integrated into the genome of the cell, for example, an endogenous locus. In some embodiments, the donor comprises a full length gene flanked by regions of homology with the targeted cleavage site. In some embodiments, the donor lacks homologous regions and is integrated into a target locus through homology independent mechanism (i.e. NHEJ). In other embodiments, the donor comprises a smaller piece of nucleic acid flanked by homologous regions for use in the cell (i.e. for gene correction). In some embodiments, the donor comprises a gene encoding a functional or structural component such as a shRNA, RNAi, miRNA or the like. In other embodiments the donor comprises a gene encoding a regulatory element that binds to and/or modulates expression of a gene of interest. According to a preferred embodiment of the invention the construct comprises an adeno-associated viral vector (AAV) and/or is encoded by a plasmid DNA.

In other aspects, the construct(s) as described herein is(are) delivered by viral and/or non-viral gene transfer methods. Additional sequences (coding or non-coding sequences) may be included in the construct, including but not limited to, sequences encoding a 2A peptide, SA site, IRES, and the like as well as additional coding sequences such as reporters, therapeutic polypeptides and the like.

In another aspect, described herein are methods of altering gene expression in a cell, the method comprising introducing into the cell a construct as described herein. In certain embodiments, the construct encodes a DNA-binding molecule (e.g., ZFP, TALE, CRISPR/Cas single guide RNA, etc.) operably linked to one or more functional domains (e.g., transcriptional repressor, transcriptional activator, or nuclease). In any of the methods described herein a donor nucleic acid may integrated into the genome of the cell, for example by creating a double-stranded break (DSB) in the genome of a cell with a nuclease as described herein such that the donor nucleic acid is integrated at the site of the DSB. In certain embodiments, the donor nucleic acid is integrated via non-homology dependent methods (e.g., NHEJ). In certain embodiments, the DSB is created by one or more zinc-finger nucleases (ZFNs), fusion proteins comprising a zinc finger binding domain, which is engineered to bind a sequence within the region of interest, and a cleavage domain or a cleavage half-domain. In other embodiments, the DSB is created by one or more TALE DNA-binding domains (naturally occurring or non-naturally occurring) fused to a nuclease domain (TALEN, mega TAL and/or cTALEN). In yet further embodiments, the DSB is created using a CRISPR/Cas nuclease system where an engineered single guide RNA or its functional equivalent is used to guide the nuclease to a targeted site in a genome.

In other aspects, the disclose provides methods of regulating expression of an exogenous gene modulator introduced into the cell, the methods comprising introducing a construct as described herein. In certain embodiments, the gene modulator represses or inactivates expression of an endogenous gene and self-regulation occurs when the gene modulator binds to the low-affinity target site in the construct (e.g., at high enough levels to be in excess of the binding capacity of the intended target site), wherein binding to the low-affinity target site modulates (e.g., represses) expression of the gene modulator and/or additional coding sequences from the construct.

In other aspects, the disclosure provides cells that are genetically modified using a construct as described herein. Any cell type can be used including, but not limited to, mammalian, plant, fungal, bacterial, fish and the like. In certain embodiments, the cells are cell lines. In other embodiments the cells are primary cells. In still further embodiments, the cells are stem cells (e.g., hematopoietic stem cells).

In some aspects, pharmaceutical compositions comprising the polypeptides, polynucleotides (e.g., self-regulating constructs) and/or cells as described herein are provided. In certain embodiments, the compositions are administered to a subject, for example, for prevention and/or treatment of a disease or disorder. The pharmaceutical compositions can be formulated for systemic administration (e.g., intravenous, intraperitoneal, intramuscular, subdermal, pulmonary or intracranial infusion) or topical application.

Also provided herein is a system for regulating expression of one or more gene modulators, the system comprising, a cell with a genome comprising an intended target site for a gene modulator and an exogenous construct comprising a low-affinity (self-regulating) target site as described herein that is operably linked to a sequence encoding the gene modulator (or component of the gene modulator, e.g., protein modulator that functions when co-expressed with a single-guide RNA). Expression of the gene modulator is itself modulated (decreased or increased) upon binding of the gene modulator to the low-affinity target site. In certain embodiments, the low-affinity target site comprises the same sequence as the intended target site. In other embodiments, the low-affinity target site comprises a different sequence than the intended target site.

A kit, comprising the constructs of the invention and/or donor molecules is also provided. The constructs may encode a ZFP-TF, a ZFN, a TALE-TF, a TALEN, MegaTAL, cTALEN and/or a CRISPR/Cas system. The kit may further comprise as described herein, donor molecules, instructions for performing the methods of the invention, and the like. The kit may also comprise donor molecules of interest such as selection or screening markers.

These and other aspects will be readily apparent to the skilled artisan in light of disclosure as a whole.

BRIEF DESCRIPTION OF THE DRAWINGS

FIG. 1A shows a construct in which protein expression is driven by the Htt promoter. FIG. 1B shows a construct in which protein expression is driven by the constitutive CMV promoter. FIG. 1C shows a construct in which the CMV promoter is modified to include 7-20 CAG repeats (SEQ ID NO: 22), which act as low-affinity target sites for CAG-binding ZFPs. FIG. 1D shows a construct in which expression is driven by the Htt promoter with non-coding exon 1 that contains 17 CAG repeats(SEQ ID NO: 23) which act as low-affinity target sites for CAG-binding ZFPs. Also shown are human beta-globin intron, a nuclear localization signal ("NLS"), the FLAG epitope tag, 2A sequences and the polyadenylation signal from the human growth hormone gene (hGH polyA).

FIGS. 6A and 6B are graphs depicting analysis of 293T cells transfected with plasmids of the indicated constructs. FIG. 6A depicts the MFI of GFP expressed in cells transfected with constructs including as shown in FIG. 1C and Example 1. As indicated (left panel), the constructs included no low-affinity Htt target sites (0) or 7, 10, 13, 15, 18 or 20 low-affinity Htt target sites in the form of CAG repeats. FIG. 6B is a graph depicting ZFP-2A-VENUS expression by quantitative Taqman® analysis of the cells transfected with the constructs described in FIG. 6A.

FIG. 7A is a graph depicting MFI Of GFP of the 293T cells transfected with the indicated constructs as described in Example 1. FIG. 7 discloses "CAG(n)=7,10,13,15,18,20" as SEQ ID NO: 28).

FIG. 8A is a graph depicting MFI of GFP expression in 293T cells transduced with the indicated constructs as described in Example 1. FIG. 8B is a graph showing Taqman® analysis of the cells for ZFP expression. FIG. 8C depicts reporter gene expression (VENUS) from the constructs comprising 0 to 20 CAG repeats(SEQ ID NO: 24), where expression is visualized through flow cytometry and by fluorescent microscopy.

FIG. 9A depicts the expression of the Htt gene from either the wild type Htt allele ("CAG17" (SEQ ID NO: 23))or a mutant (disease-associated) Htt allele ("CAG48" (SEQ ID NO: 25)) in the presence of AAV with CAG binding 33074 or control 5475 ZFP in the promoter constructs as described in Example 1. FIG. 9B shows the ZFP TF expression measured by quantitative Taqman® analysis of the neurons transduced with the constructs described in FIG. 9A.

DETAILED DESCRIPTION

Figure 1A:
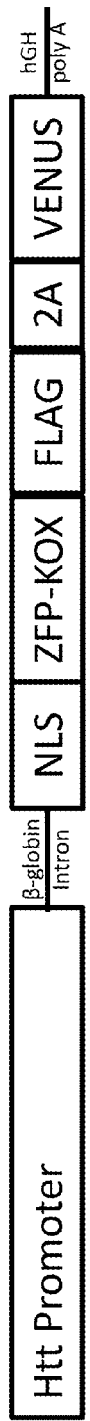
FIGS. 1A to 1D are schematics depicting constructs comprising ZFP repressors ("ZFP-KOX") and GFP variant Venus ("VENUS"). KOX refers to the KRAB repression domain from the KOX1 protein.

Disclosed herein are compositions and methods for regulating expression of an exogenous gene modulator within a cell. In particular, the present invention concerns constructs encoding one or more engineered gene modulators (e.g., transcription factors and/or nucleases) in which expression of the engineered gene modulator can be regulated by inclusion of one or more low-affinity target sites for the transcription factor or nuclease. For example, low-affinity target sites are included within the promoter driving expression of the gene modulator. In this way, when the transcription factor or nuclease is expressed at high enough levels within the cell (e.g., over-expressed), the low-affinity target sites are bound by the gene modulator and expression of the gene modulator is modulated (down-regulated in the case of TF-repressors or nucleases and up-regulated in the case of TF-activators). In some embodiments, expression of a transgene of interest may also be also modulated by creating a fusion transgene such that the fusion transgene encodes both the gene modulator and a gene of interest. The invention further concerns cells comprising the constructs as described herein and pharmaceutically compositions comprising the constructs and/or cells as described herein.

Thus, the compositions and methods of the invention result in modulation of the coding sequences on the constructs, including down-regulation of gene modulator expression within a cell where over-expression is not desired and/or deleterious to the cell.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526; 6,140,081; 6,453,242; 6,534,261 and 8,586,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; 8,586, 526; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g., Swarts et al, (2014) *Nature* 507(7491):258-261; G. Sheng et al., (2013) *Proc. Natl. Acad. Sci. U.S.A.* 111, 652). A "TtAgo system" is all the components required including, for example, guide DNAs for cleavage by a TtAgo enzyme. "Recombination" refers to a process of exchange of genetic information between two polynucleotides, including but not limited to, donor capture by non-homologous end joining (NHEJ) and homologous recombination. For the purposes of this disclosure, "homologous recombination(HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e, the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide. In any of the methods described herein, additional pairs of zinc-finger proteins or TALEN can be used for additional double-stranded cleavage of additional target sites within the cell.

The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,914,796; 8,034,598; 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. An "intended" target site is one that the DNA-binding molecule is designed and/or selected to bind to (see, e.g., Table 2).

A "low-affinity" or "self-regulating" target site or target sequence is a nucleic acid sequence that is bound by a binding molecule (e.g., gene modulator) when there is an excess of the binding molecule present and/or that is bound by a binding molecule with lower binding affinity than the intended target site. A low affinity (self-regulating) target site may differ from the intended target site by 0, 1, 2, 3, 4, 5, 6 or more base pairs and/or may comprise the intended target site, for example, target sites that include additional or fewer base pairs as compared to the intended target site (e.g., may include additional repeats such as CAG or CCG). In certain embodiments, for example when the low-affinity target site comprises the same sequence as the intended target site, the low-affinity target site is bound only when there is an excess of the binding molecule present (i.e., when the intended target sites (e.g., endogenous target sites) are all bound by the binding molecule). The term also includes portions of a target site, for example repeats of a motif present in a target site.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylates, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins, for example, a fusion between a DNA-binding domain (e.g., ZFP, TALE and/or meganuclease DNA-binding domains) and a nuclease (cleavage) domain (e.g., endonuclease, meganuclease, etc. and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "multimerization domain," (also referred to as a "dimerization domain" or "protein interaction domain") is a domain incorporated at the amino, carboxy or amino and carboxy terminal regions of a ZFP TF or TALE TF. These domains allow for multimerization of multiple ZFP TF or TALE TF units such that larger tracts of trinucleotide repeat domains become preferentially bound by multimerized ZFP TFs or TALE TFs relative to shorter tracts with wild-type numbers of lengths. Examples of multimerization domains include leucine zippers. Multimerization domains may also be regulated by small molecules wherein the multimerization domain assumes a proper conformation to allow for interaction with another multimerization domain only in the presence of a small molecule or external ligand. In this way, exogenous ligands can be used to regulate the activity of these domains.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain (ZFP, TALE) is fused to a cleavage domain (e.g., endonuclease domain such as FokI, meganuclease domain, etc.), the DNA-binding domain and the cleavage domain are in operative linkage if, in the fusion polypeptide, the DNA-binding domain portion is able to bind its target site and/or its binding site, while the cleavage (nuclease) domain is able to cleave DNA in the vicinity of the target site. The nuclease domain may also exhibit DNA-binding capability (e.g., a nuclease fused to a ZFP or TALE domain that also can bind to DNA). Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

A "vector" or "construct" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any patient or subject (e.g. mammalian) to which the cells or stem cells of the invention can be administered.

DNA-Binding Domains

The constructs as described herein and cells comprising these constructs include sequences encoding one or more DNA-binding domains that specifically bind to a target sequence in any endogenous gene. Any DNA-binding domain can be used in the compositions and methods disclosed herein, including but not limited to a zinc finger DNA-binding domain, a TALE DNA binding domain, a DNA-binding domain from a meganuclease or a single-guide RNA (e.g., CRISPR/Cas system).

In certain embodiments, the DNA binding domain comprises a zinc finger protein. Preferably, the zinc finger protein is non-naturally occurring in that it is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in U.S. Pat. No. 6,794,136.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

Selection of target sites and methods for design and construction of fusion proteins (and polynucleotides encoding same) are known to those of skill in the art and described in detail in U.S. Pat. Nos. 8,586,526; 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

The ZFPs can also be fusion proteins that include one or more regulatory domains, which domains can be transcriptional activation or repression domains. In some embodiments, the fusion protein comprises two ZFP DNA binding domains linked together. These zinc finger proteins can thus comprise 8, 9, 10, 11, 12 or more fingers. In some embodiments, the two DNA binding domains are linked via an extendable flexible linker such that one DNA binding domain comprises 4, 5, or 6 zinc fingers and the second DNA binding domain comprises an additional 4, 5, or 5 zinc fingers. In some embodiments, the linker is a standard inter-finger linker such that the finger array comprises one DNA binding domain comprising 8, 9, 10, 11 or 12 or more fingers. In other embodiments, the linker is an atypical linker such as a flexible linker. The DNA binding domains are fused to at least one regulatory domain and can be thought of as a 'ZFP-ZFP-TF' architecture. Specific examples of these embodiments can be referred to as "ZFP-ZFP-KOX" which comprises two DNA binding domains linked with a flexible linker and fused to a KOX repressor and "ZFP-KOX-ZFP-KOX" where two ZFP-KOX fusion proteins are fused together via a linker.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

"Two handed" zinc finger proteins are those proteins in which two clusters of zinc finger DNA binding domains are separated by intervening amino acids so that the two zinc finger domains bind to two discontinuous target sites. An example of a two handed type of zinc finger binding protein is SIP1, where a cluster of four zinc fingers is located at the amino terminus of the protein and a cluster of three fingers is located at the carboxyl terminus (see Remacle et al, (1999) *EMBO Journal* 18 (18): 5073-5084). Each cluster of zinc fingers in these proteins is able to bind to a unique target sequence and the spacing between the two target sequences can comprise many nucleotides. Two-handed ZFPs may include a functional domain, for example fused to one or both of the ZFPs. Thus, it will be apparent that the functional domain may be attached to the exterior of one or both ZFPs or may be positioned between the ZFPs (attached to both ZFPs). See, e.g., U.S. Patent Publication No. 20130253940.

In certain embodiments, the DNA-binding domain comprises a naturally occurring or engineered (non-naturally occurring) TAL effector (TALE) DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et at (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et at (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et at (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS 1000 (See Heuer et at (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TALEs depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TALE's target sequence (see Moscou and Bogdanove, (2009) *Science* 326:1501 and Boch et at (2009) *Science* 326:1509-1512). Experimentally, the code for DNA recognition of these TALEs has been determined such that an HD sequence at positions 12 and 13 leads to a binding to cytosine (C), NG binds to T, NI to A, C, G or T, NN binds to A or G, and IG binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). Christian et at ((2010)< *Genetics* epub 10.1534/genetics.110.120717). In addition, TALENs with C- and/or N-terminal truncations (C-cap and/or N-cap sequences) and atypical repeat variable diresidue regions (RVDs) have also been described. See, U.S. Pat. No. 8,586,526, incorporated by reference in its entirety.

Methods and compositions for engineering these TALEN proteins for robust, site specific interaction with the target sequence of the user's choosing have been published (see U.S. Pat. No. 8,586,526). In some embodiments, the TALEN comprises a endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et at (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs).

Fusion Molecules

Fusion molecules (e.g., fusion proteins) comprising DNA-binding domains (e.g., ZFPs, TALEs, single guide) as described herein and a heterologous regulatory (functional) domain (or functional fragment thereof) are also provided.

Common functional domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Pat. Nos. 8,586,526; 7,888,121; 8,409,861; and 7,972,854 for details regarding fusions of DNA-binding domains and nuclease cleavage domains, incorporated by reference in their entireties herein Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Bark *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1 and a modified Cas9 transactivator protein. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; Hobo et al. (1999) *Proc. Natl. Acad. Sci. USA* 96:15,348-15,353; and Perez-Pinera et al. (2013) *Nature Methods* 10:973-976).

It will be clear to those of skill in the art that, in the formation of a fusion molecule (or a nucleic acid encoding a fusion protein) between a DNA-binding domain as described herein and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in U.S. Pat. Nos. 6,919,204 and 7,053,264.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., single-guide RNA, antibiotic, intercalator, minor groove binder, nucleic acid) on the other, are constructed by methods of known to those of skill in the art, including, but not limited to, biochemical conjugation, co-expression in a cell and the like.

In certain embodiments, the target site bound by the DNA binding domain (e.g., intended target site and/or low affinity site) is present in and/or near control element, for example within, adjacent or near, an endogenous control element or the control element (e.g., promoter) driving expression of the exogenous gene modulator in the host cell. In certain embodiments, the target site is an accessible region of cellular chromatin. Accessible regions can be determined as described, for example, in U.S. Pat. No. 6,511,808. If the target site is not present in an accessible region of cellular chromatin, one or more accessible regions can be generated as described in U.S. Pat. No. 7,001,768.

The fusion molecules as described herein may be formulated with a pharmaceutically acceptable carrier, as is known to those of skill in the art. See, for example, Remington's Pharmaceutical Sciences, 17th ed., 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Functional domains that are regulated by exogenous small molecules or ligands may also be selected. For example, RheoSwitch® technology may be employed wherein a functional domain only assumes its active conformation in the presence of the external RheoChem™ ligand (see for example US 20090136465). Thus, the DNA-binding domain (e.g., ZFP or TALE or single-guide) may be operably linked to the regulatable functional domain wherein the resultant activity of the gene modulator (e.g., ZFP-TF or TALE-TF or CRISPR/Cas-TF) is controlled by the external ligand.

Nucleases

In certain embodiments, the fusion molecule comprises a DNA-binding binding domain and cleavage (nuclease) domain. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. (see, Chames et al. (2005) Nucleic Acids Res 33(20):e178; Arnould et al. (2006) J. Mol. Biol. 355:443-458). In addition, engineering of ZFPs and TALEs has also been described. See, e.g., U.S. Pat. Nos. 8,586,526; 6,534,261; 6,607,882; 6,824,978; 6,979,539; 6,933,113; 7,163,824; and 7,013,219.

In addition, ZFPs and TALEs have been fused to nuclease domains to create ZFNs and TALENs—functional entities that are able to recognize their intended nucleic acid target through their engineered (ZFP or TALE) DNA binding domains and cause the DNA to be cut near the ZFP or TALE DNA binding site via the nuclease activity. See, e.g., Kim et al. (1996) Proc Natl Acad Sci USA 93(3):1156-1160. More recently, ZFNs have been used for genome modification in a variety of organisms. See, for example, See, e.g., U.S. Pat. Nos. 8,623,618; 8,034,598; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20060063231; 20080159996; 201000218264; 20120017290; 20110265198; 20130137104; 20130122591; 20130177983 and 20130177960.

Thus, the methods and compositions described herein are broadly applicable and may involve any nuclease of interest. Non-limiting examples of nucleases include meganucleases, TALENs, Ttago nucleases, CRISPR/Cas nuclease systems and zinc finger nucleases. The nuclease may comprise heterologous DNA-binding and cleavage domains (e.g., zinc finger nucleases; TALENs; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In certain embodiments, the composition comprises a DNA-binding domain and/or nuclease (cleavage) domain from a meganuclease (homing endonuclease). Naturally-occurring meganucleases recognize 15-40 base-pair cleavage sites and are commonly grouped into four families: the LAGLIDADG (SEQ ID NO: 26) family, the GIY-YIG family, the His-Cyst box family and the HNH family. In certain embodiments, the homing endonuclease (meganuclease) is engineered (non-naturally occurring). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

DNA-binding domains from naturally-occurring meganucleases, primarily from the LAGLIDADG (SEQ ID NO: 26) family, have been used to promote site-specific genome modification in plants, yeast, Drosophila, mammalian cells and mice, but this approach has been limited to the modification of either homologous genes that conserve the meganuclease recognition sequence (Monet et al. (1999), Biochem. Biophysics. Res. Common. 255: 88-93) or to pre-engineered genomes into which a recognition sequence has been introduced (Route et al. (1994), Mol. Cell. Biol. 14:8096-106; Chilton et al. (2003) Plant Physiology 133: 956-65; Puchta et al. (1996), Proc. Natl. Acad. Sci. USA 93: 5055-60; Rong et al. (2002), Genes Dev. 16: 1568-81; Gouble et al. (2006), J. Gene Med. 8(5):616-622). Accordingly, attempts have been made to engineer meganucleases to exhibit novel binding specificity at medically or biotechnologically relevant sites (Porteus et al. (2005), Nat. Biotechnol. 23: 967-73; Sussman et al. (2004), J. Mol. Biol. 342: 31-41; Epinat et al. (2003), Nucleic Acids Res. 31: 2952-62; Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI).

In other embodiments, the nuclease is a zinc finger nuclease (ZFN). ZFNs comprise a zinc finger protein that has been engineered to bind to a target site in a gene of choice and cleavage domain or a cleavage half-domain.

As described in detail above, zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in U.S. Pat. No. 6,794,136.

In addition, as disclosed in these and other references, DNA-binding domains (e.g., zinc finger proteins, TALE proteins, etc.) may be linked together or to functional domains using any suitable linker sequences. See, e.g., U.S. Pat. Nos. 8,772,453; 6,479,626; 6,903,185; and 7,153,949 U.S. Patent Publication No. 20090305419; and U.S. application Ser. No. 14/471,782.

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et at (2012) *Science* 337, p. 816-821, Jinek et al, (2013), *eLife* 2:e00471, and David Segal, (2013) *eLife* 2:e00563). Thus, the CRISPR/Cas system can be engineered to create a DSB at a desired target in a genome, and repair of the DSB can be influenced by the use of repair inhibitors to cause an increase in error prone repair.

Nucleases as described herein also comprise a nuclease (cleavage domain, cleavage half-domain). As noted above, the cleavage domain may be heterologous to the DNA-binding domain, for example a zinc finger DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion molecules are required for cleavage if the fusion molecules comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger- or TALE-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger- or TALE-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 20070134796, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,888,121; 8,409,861; 7,914,796; and 8,034,598, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains. Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Pat. Nos. 7,888,121; 8,409,861; 7,914,796; and 8,034,598 and U.S. Patent Publication No. 20120040398, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Pat. No. 8,623,618).

Engineered cleavage half-domains described herein can be prepared using any suitable method, for example, by site-directed mutagenesis of wild-type cleavage half-domains (Fok I) as described in U.S. Pat. Nos. 7,888,121 and 7,914,796.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

In some embodiments, the DNA binding domain is an engineered domain from a TAL effector similar to those derived from the plant pathogens *Xanthomonas* (see Boch et al, (2009) *Science* 326: 1509-1512 and Moscou and Bogdanove, (2009) *Science* 326: 1501) and *Ralstonia* (see Heuer et at (2007) *Applied and Environmental Microbiology* 73(13): 4379-4384). Also, U.S. Pat. No. 8,586,526.

Nucleases (e.g., ZFNs or TALENs) can be screened for activity prior to use, for example in a yeast-based chromosomal system as described in U.S. Pat. No. 8,563,314. Nuclease expression constructs can be readily designed using methods known in the art. See, e.g., U.S. Pat. Nos. 7,888,121 and 8,409,861 and U.S. Patent Publication Nos. 20030232410; 20050208489; 20050026157; 20060063231; and 20070134796. Expression of the nuclease may be under the control of a constitutive promoter or an inducible promoter, for example the galactokinase promoter which is activated (de-repressed) in the presence of raffinose and/or galactose and repressed in presence of glucose.

In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains), or a generic nuclease guided by a specific guide RNA (e.g. a CRPISR/Cas).

Target Sites

The constructs described herein also include one or more low-affinity target sites for the DNA-binding domain. As noted above, a low-affinity target site is one that is typically bound by the DNA-binding domain of the gene modulator when there is an excess of the gene modulator present and/or when the DNA-binding domain binds with lower affinity than to the intended target site (against which the DNA-binding domain is designed and tested). Binding affinity can be determined by any suitable means, either including, but not limited to, Kd analysis or functional analysis on reporter or endogenous genes (e.g., measuring levels of gene expression or cleavage). Binding affinity can be expressed quantitatively (e.g., Kd, gene expression or cleavage levels) or qualitatively (e.g., relative to other binding domains, including those that bind to the same or different target sequence within the same gene).

As noted above, the target sites for the transcription factors and/or nucleases of the constructs disclosed herein typically include a plurality of binding sites (e.g., 2, 3, 4, 5, 6, 7, 8, 9, 10, 11, 12, 13, 14, 15, 16, 17, or more). For instance, ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides, where each zinc finger of the multi-finger protein binds to a 3 base pair target subsite with optional unbound nucleotides within the overall target site. Similarly, target sites bound by TALE DNA-binding proteins include any number of nucleotides in which 1-2 nucleotides are bound by the repeat variable diresidue (RVD) of a single TALE repeat (or half-repeat). See, e.g., U.S. Pat. No. 8,586,526.

DNA-binding molecules are designed and/or selected to bind to an intended target site. See, e.g., Table 2. Nonetheless, when expressed at high enough levels, these DNA-binding molecules may bind to less preferred, low-affinity target sites. The self-regulating constructs as described herein make use of this phenomena by providing low-affinity target sites that drive expression of the gene modulator (repressor or nuclease) such that, when expressed at high enough levels, the gene modulator binds to the low-affinity site present in the promoter. Binding of the gene modulator (repressor or nuclease) to the low-affinity target site in turn represses expression of the gene modulator, thereby providing a self-regulating construct.

The sequence of the low-affinity target site is typically not identical to the sequence of the intended target site. One or more nucleotides including all the nucleotides can be altered. In certain embodiments, the low-affinity target site includes at least half of the same base pairs (contiguous or non-contiguous) as the intended target site. In other embodiments, the low-affinity target site includes at least 60%, 70%, 80%, 85%, 90%, 95% or 99% of the same base pairs as the intended target site. For example, in a target site of 18 base pairs, 0, 1, 2, 3, 4, 5, 6, 7, 8, 9, 10, 11, 12, 13, 14, 15, 16, 17 base pairs may be different as between the low-affinity target site and the intended target site. Similarly, for an intended target site of 21 base pairs, 0, 1, 2, 3, 4, 5, 6, 7, 8, 9, 10, 11, 12, 13, 14, 15, 16, 17 18, 19, or 20 base pairs may be different in the low-affinity target site may be different from the intended target site. In certain embodiments, the low-affinity target site may include contiguous sequences (e.g., portions) (repeated or not) of target subsites found in the intended target site, for example CAG or CCG repeats as found in modulators of genes involved in trinucleotide repeat disorders. In certain embodiments, the low-affinity target site and intended target sites are the same but the target subsites bound by the DNA-binding domain are not contiguous.

Any number of low-affinity target sites (or portions thereof) can be included in the construct. In certain embodiments, the low-affinity target site includes one or more repeats of a motif found in the intended target sequence, for example CAG or CCG repeats found in modulators that bind to mutant and/or wild-type alleles found in subjects with trinucleotide repeat disorders. Thus, the number of low-affinity target sites included in the construct can be readily determined by the skilled artisan depending on the amount or extent of self-regulation desired. For instance, for regulation of a modulator with strong binding affinity for the intended target site, fewer low-affinity target sites can be included than for modulators with lower binding affinity for their intended target site. See, Examples below.

Donors

As noted above, insertion of an exogenous sequence (also called a "donor sequence" or "donor" or "transgene") can be performed using the gene modulators (e.g., nucleases) as described herein, for example for correction of a mutant gene or for increased expression of a wild-type gene. It will be readily apparent that the donor sequence need not be identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest or, alternatively, a donor molecule may be integrated into a cleaved target locus via non-homologous end joining (NHEJ) mechanisms. See, e.g., U. See, e.g., U.S. Pat. Nos. 7,888,121 and 7,972,843 and U.S. Pat. No. 8,703,489 and U.S. Publication Nos. 20110281361 and 20110207221

Described herein are methods of targeted insertion of any polynucleotides for insertion into a chosen location. Polynucleotides for insertion can also be referred to as "exogenous" polynucleotides, "donor" polynucleotides or molecules or "transgenes." The donor polynucleotide can be DNA, single-stranded and/or double-stranded and can be introduced into a cell in linear or circular (e.g., minicircle) form. See, e.g., U.S. Pat. No. 8,703,489 and U.S. Publication Nos. 20110281361 and 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 1 target site, for example, for use with a CRISPR/Cas, or 2 target sites, for example for a pair of ZFNs and/or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into a selected locus such that some or none of the endogenous sequences are expressed, for example as a fusion with the transgene. In other embodiments, the transgene is integrated into any endogenous locus, for example a safe-harbor locus. Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type beta globin gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions. In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The proteins (e.g., ZFPs, TALEs, CRISPR/Cas), polynucleotides encoding same and compositions comprising the proteins and/or polynucleotides described herein may be delivered to a target cell by any suitable means including, for example, by injection of ZFP-TF, TALE-TF proteins or by use of ZFN or TALEN encoding mRNA or by co-introduction of polynucleotides (e.g., single guide RNAs) and associated functional domains (e.g., activation, repression, nuclease, etc.)

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line.

Suitable cells also include stem cells such as, by way of example, embryonic stem cells, induced pluripotent stem cells, hematopoietic stem cells, neuronal stem cells and mesenchymal stem cells.

Methods of delivering proteins comprising zinc finger proteins as described herein are described, for example, in U.S. Pat. Nos. 8,586,526, 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the compositions described herein. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979, 539; 7,013,219; and 7,163,824, incorporated by reference herein in their entireties. Furthermore, it will be apparent that any of these vectors may comprise one or more zinc finger or TALE protein-encoding sequences. Thus, when one or more ZFPs, TALEs or CRISPR/Cas polynucleotides and/or proteins are introduced into the cell, the sequences encoding the ZFPs, TALEs or CRISPR/Cas proteins may be carried on the same vector or on different vectors. When multiple vectors are used, each vector may comprise a sequence encoding one or multiple ZFPs, TALEs or CRISPR/Cas systems.

Conventional viral and non-viral based gene transfer methods can be used to introduce nucleic acids encoding engineered ZFPs, TALEs, Ttago and/or CRISPR/Cas systems in cells (e.g., mammalian cells) and target tissues. Such methods can also be used to administer nucleic acids encoding ZFPs, TALEs, Ttago and/or a CRISPR/Cas system to cells in vitro. In certain embodiments, nucleic acids encoding the ZFPs, TALEs, Ttago and/or CRISPR/Cas system are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, naked RNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See US patents U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™ and Lipofectamine™ RNAiMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) *Nature Biotechnology* 27(7):643).

The use of RNA or DNA viral based systems for the delivery of nucleic acids encoding engineered ZFPs, TALEs or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs, TALEs or CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon mouse leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, Human *Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Vectors suitable for introduction of polynucleotides described herein also include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 20090117617.

Recombinant adeno-associated virus vectors (rAAV) may also be used to deliver the compositions described herein. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8AAV 8.2, AAV9, and AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney mouse leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, intrathecal, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP, TALE or CRISPR/Cas system nucleic acid (gene. cDNA or mRNA), and re-infused back into the subject organism (e.g., patient). In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein in their entireties. Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+ (panB cells), GR-1 (granulocytes), and Iad (differentiated antigen presenting cells) (see Inaba et al., *J. Exp. Med.* 176:1693-1702 (1992)).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific TALENs or ZFNs (see, U.S. Patent Publication No. 20100003756) in the stem cells, or those that are disrupted in a caspase, again using caspase-6 specific ZFNs for example. These cells can be transfected with the ZFP TFs or TALE TFs that are known to regulate mutant or wild-type Htt.

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

In certain embodiments, the compositions (including fusion proteins, CRISPR/Cas systems and/or modified cells) as described herein (e.g., polynucleotides and/or proteins) are delivered directly in vivo. The compositions (cells, polynucleotides and/or proteins) may be administered directly into the CNS, including but not limited to direct injection into the brain or spinal cord. One or more areas of the brain may be targeted, including but not limited to, the hippocampus, the substantia nigra, the nucleus basalis of Meynert (NBM), the striatum and/or the cortex. Alternatively or in addition to CNS delivery, the compositions may be administered systemically (e.g., intravenous, intraperitoneal, intracardial, intramuscular, intrathecal, subdermal, and/or intracranial infusion). Methods and compositions for delivery of compositions as described herein directly to a subject (including directly into the CNS) include but are not limited to direct injection (e.g., stereotactic injection) via needle assemblies. Such methods are described, for example, in U.S. Pat. Nos. 7,837,668; 8,092,429, relating to a needle assembly for delivery of compositions to the brain and U.S. Patent Publication No. 20060239966, incorporated herein by reference in their entireties.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), any plant cell (differentiated or undifferentiated) as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the gene modulators (e.g. ZFNs or TALENs) or gene modulator systems (e.g., Ttago and/or CRISPR/Cas). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see, Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+ (panB cells), GR-1 (granulocytes), and Iad (differentiated antigen presenting cells) (see Inaba et al., J. Exp. Med. 176:1693-1702 (1992)).

Stem cells that have been modified may also be used in some embodiments. For example, stem cells that have been made resistant to apoptosis may be used as therapeutic compositions where the stem cells also contain the ZFPs, TALEs, ZFNs, TALENs, CRISPR/Cas systems and/or donors of the invention. Resistance to apoptosis may come about, for example, by knocking out BAX and/or BAK using BAX- or BAK-specific nucleases (see, U.S. Patent Publication No. 2010/0003756) in the stem cells, or those that are disrupted in a caspase, again using caspase-6 specific ZFNs for example. Alternatively, resistance to apoptosis can also be achieved by the use of caspase inhibitors like Z-VAD-FMK (carbobenzoxy-valyl-alanyl-aspartyl-[O-methyl]-fluoromethylketone).

Vectors (e.g., retroviruses, adenoviruses, liposomes, etc.) containing therapeutic ZFPs, TALEs, ZFNs, TALENs, CRISPR/Cas system and/or donor nucleic acids can also be administered directly to an organism for transduction of cells in vivo. Alternatively, naked DNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

The following Examples relate to exemplary embodiments of the present disclosure in which the composition comprises a zinc finger transcription factor repressor (ZFP-TF repressor). It will be appreciated that this is for purposes of exemplification only and that other compositions can be used, for instance ZFP-TF activators, zinc finger nucleases (ZFNs), TALE-TFs (activators or repressors), TALENs (e.g. standard TALENs, Mega-TALs and/or compact TALENs (cTALENs)), CRISPR/Cas systems (transcription factors and/or nuclease systems), homing endonucleases (meganucleases) with engineered DNA-binding domains and/or fusions of naturally occurring of engineered homing endonucleases (meganucleases) DNA-binding domains and heterologous cleavage domains and/or fusions of meganucleases, zinc finger and/or TALE proteins. Further, for the purposes of exemplification only, regulation of Htt alleles is exemplified where the self regulating promoters contained multiple targets of the CAG-binding proteins, but it will be appreciated that the methods and compositions of the invention can be carried out using any low-affinity target site(s) in the expression construct, resulting in the same self-regulation.

EXAMPLES

Example 1

Constructs

Figure 1B:
Figure 1C:
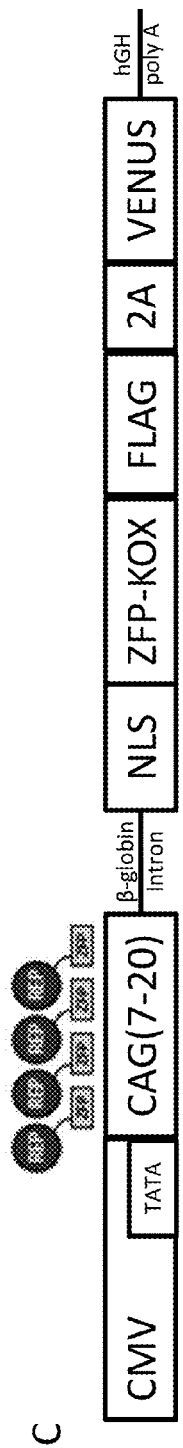
Figure 1D:

Adeno-associated viral vectors (AAV), lentiviral (LV) and integration defective lentiviral (IDLV) constructs (Hong et al. (2002) Science. 295(5556):868-72 expressing Htt-binding ZFPs (see U.S. Patent Publication No. 20130253040) and GFP Venus variant (Nagai et al. (2002) Nature Biotech. 20(1):87-90) were generated with the ZFP encoding sequence operably linked to an Htt promoter sequence (FIG. 1A), a CMV promoter (FIG. 1B), a modified CMV promoter in which CAG repeats (7 to 20)(SEQ ID NO: 22) were cloned into the CMV promoter downstream of the TATA box (FIG. 1C, also referred to as the "self-regulating promoter construct" or "low-affinity target site construct"), and a modified Htt promoter with non-coding exon 1 that contains 17 CAG repeats which act as low-affinity target sites for CAG-binding ZFPs (FIG. 1D).

The ZFP designs and target sites are shown below in Tables 1 and 2. ZFPs are linked to the KRAB repression domain of KOX1. ZFPs designated 32528 and 31809 bind to the promoter of Htt and represses transcription from both mutant and wild-type Htt alleles. ZFPs designated 33074, 30640 and 30648 are designed to bind to CAG repeats; 30648 can bind to CAG repeats on both mutant and wild-type Htt alleles and repress transcription of both; 30640 and 33074 preferentially bind the expanded CAG repeats and selectively repress transcription of mutant Htt. The ZFP designated 5475 is a control ZFP that is designed to bind to the Chk2 gene and does not bind to CAG repeats In Table 2, nucleotides in the target site that are contacted by the ZFP recognition helices are indicated in uppercase letters; non-contacted nucleotides indicated in lowercase.

TABLE 1

Zinc Finger Designs

| SBS # | Design | | | | | |
|---|---|---|---|---|---|---|
| | F1 | F2 | F3 | F4 | F5 | F6 |
| 33074 | RSDNLSE (SEQ ID NO: 1) | KRCNLRC (SEQ ID NO: 2) | QSGDLTR (SEQ ID NO: 3) | QSGDLTR (SEQ ID NO: 3) | RSDNLSE (SEQ ID NO: 1) | KRCNLRC (SEQ ID NO: 2) |
| 30648 | RSDNLSE (SEQ ID NO: 1) | KRCNLRC (SEQ ID NO: 2) | RSDNLSE (SEQ ID NO: 1) | KRCNLRC (SEQ ID NO: 2) | RSDNLSE (SEQ ID NO: 1) | KRCNLRC (SEQ ID NO: 2) |

TABLE 1-continued

Zinc Finger Designs

| SBS # | F1 | F2 | F3 | F4 | F5 | F6 |
|---|---|---|---|---|---|---|
| 30640 | QSSDLSR (SEQ ID NO: 4) | QWSTRKR (SEQ ID NO: 5) | QSSDLSR (SEQ ID NO: 4) | QWSTRKR (SEQ ID NO: 5) | QSGDLTR (SEQ ID NO: 3) | NA |
| 32528 | QSGHLQR (SEQ ID NO: 6) | TSGNLTR (SEQ ID NO: 7) | QSGDLTR (SEQ ID NO: 3) | DRSHLAR (SEQ ID NO: 8) | RSDVLST (SEQ ID NO: 9) | VRSRLRR (SEQ ID NO: 10) |
| 31809 | RSDDLSR (SEQ ID NO: 11) | RNDNRTK (SEQ ID NO: 12) | RSDDLTR (SEQ ID NO: 13) | RSDDRKT (SEQ ID NO: 14) | RSDDLTR (SEQ ID NO: 13) | QSSDLRR (SEQ ID NO: 15) |

TABLE 2

Target sites

| SBS # | Target Site |
|---|---|
| 33074 | agCAGCAGcaGCAGCAgCAGCAGcagca_(SEQ ID NO: 16) |
| 30648 | agCAGCAGCAGCAGCAGCAGcagcagca_(SEQ ID NO: 16) |
| 30640 | caGCAGCAGCAGCAGCAgcagcagcagc_(SEQ ID NO: 17) |
| 32528 | ccGGGACGGGTCCAaGATGGAcggccgc_(SEQ ID NO: 18) |
| 31809 | acGCTGCGCCGGCGGAGGCGggccgcg_(SEQ ID NO: 19) |

Example 2

Htt and CMV Promoter-Driven Constructs

Figure 2:
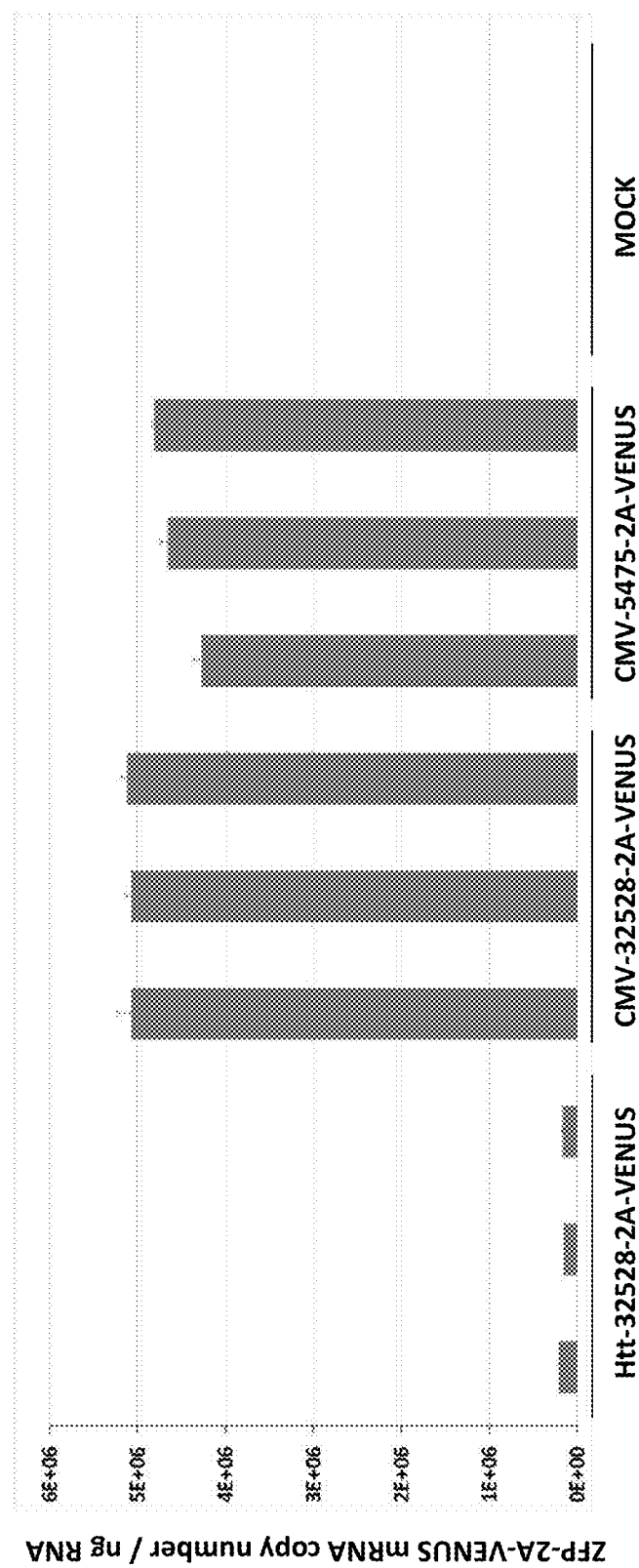
FIG. 2 is a graph depicting expression of the ZFP-2A-Venus mRNA copy number in Huntington's Disease (HD) neurons infected with LV comprising the indicated constructs. The ZFPs used in the constructs are the Htt or control (Chk2) binding proteins as described in Example 1.
Figure 3:
FIG. 3 is a graph depicting relative Htt expression measured by quantitative RT-PCR (qRT-PCR) in HD neurons infected with the indicated LV constructs.

HD-Neurons were infected with the constructs LV-CMV-ZFP-2A-VENUS or LV-Http-ZFP-2A-VENUS and the cells harvested 21 days post infection (FIGS. 2 and 3). In addition, 293T cells were infected with the IDLV constructs with the different promoters (CMV or Htt) (FIG. 4) or transfected with expression plasmids (FIG. 5). The 293T cells were harvested 48 hours post-transduction or transfection and GFP/VENUS expression was analyzed by flow cytometry (Gauva). Quantitative RT-PCR (qRT-PCR) was also performed to measure the mRNA expression levels of Htt and/or ZFP-2A-VENUS.

For a ZFP that targets the Htt promoter (32528), the Htt promoter-driven construct resulted in lower ZFP mRNA expression (compare to the CMV promoter-driven construct, FIG. 2), and consequently less repression of endogenous Htt (FIG. 3) in HD neurons.

Figure 4:
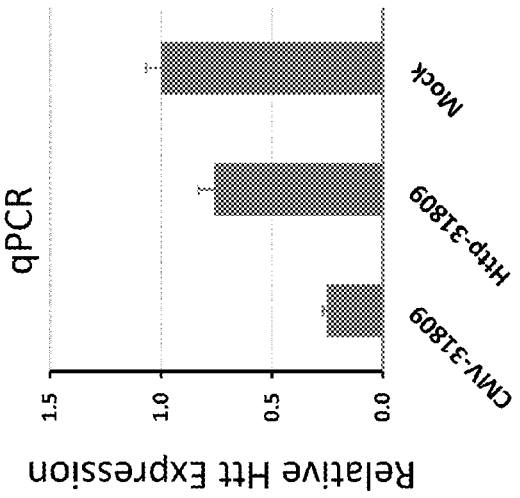
FIG. 4 is a graph depicting relative Htt expression measured by quantitative RT-PCR (qRT-PCR) in 293T cells infected with the indicated IDLV constructs.
Figure 5:
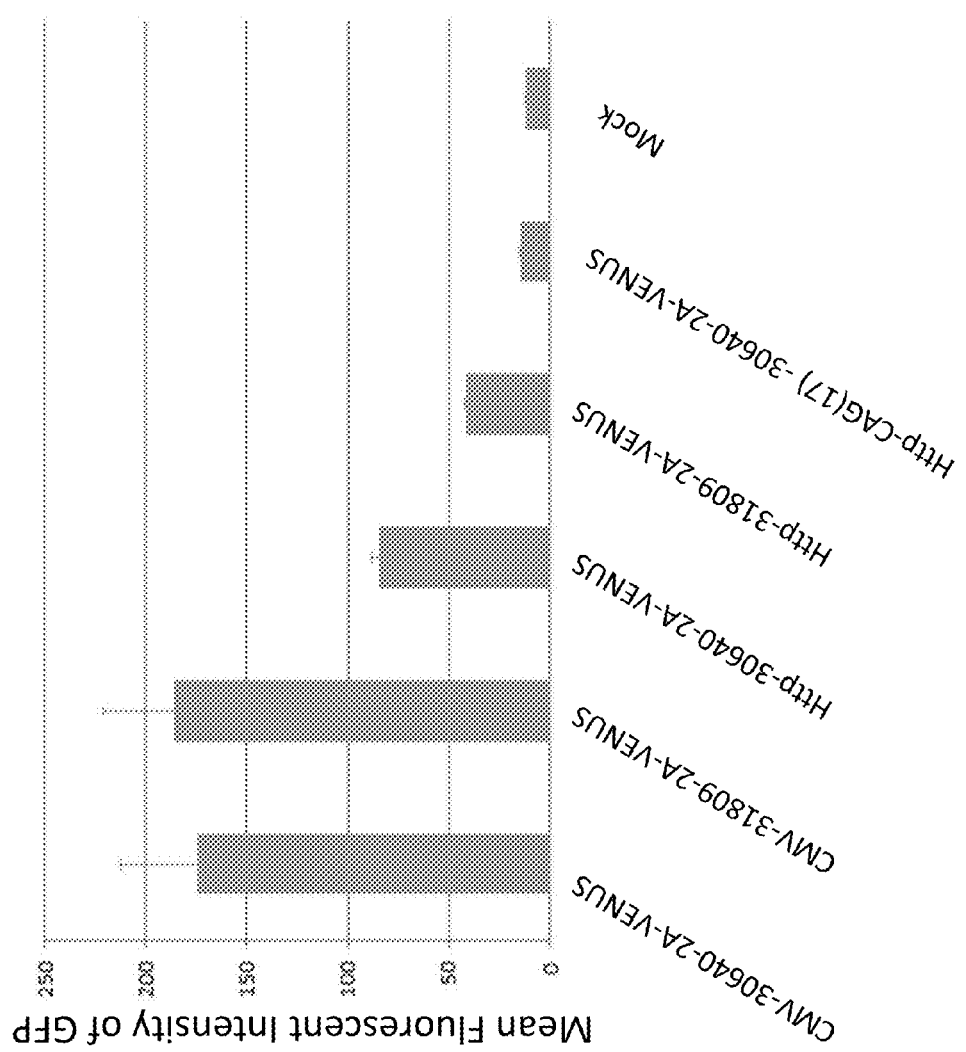
FIG. 5 is a graph depicting mean fluorescent intensity (MFI) of 293T cells transfected with plasmid with the CMV promoter, the Htt promoter (Http) or the Htt promoter and exon 1 with a CAG repeat of 17 (SEQ ID NO: 23) (Http-CAG17).

For a different ZFP that also targets the Htt promoter (31809), the Htt promoter-driven construct also resulted in less repression of endogenous Htt when compared to the CMV promoter-driven construct (FIG. 4).

The expression levels of ZFP-2A-VENUS driven by different promoters were measured by mean fluorescence intensity (MFI) of transfected cells (shown in FIG. 5). ZFP 30640 binds to CAG repeats while ZFP 31089 binds to a non-CAG target site in the Htt promoter. For the CMV promoter constructs, the expression levels of 30640-2A-VENUS and 31809-2A-VENUS were similar. For the Htt promoter constructs, 31809-2A-VENUS was expressed at a lower level compare to 30640-2A-VENUS, suggesting that ZFP 31809 down-regulates its expression through its target site in the Htt promoter. On the other hand, the expression level of 30640-2A-VENUS is reduced when it is expressed from a Htt promoter that also includes 17 CAG repeats, (SEQ ID NO: 23), suggesting that ZFP 30640 regulate its own expression through the CAG repeats.

Example 3

Self-Regulating Constructs with a Modified CMV Promoter

Constructs containing low-affinity target sites engineered into the CMV promoter construct (FIG. 1C) were also evaluated where a varying number of CAG repeats were included downstream of the CMV promoter.

Figure 6B:
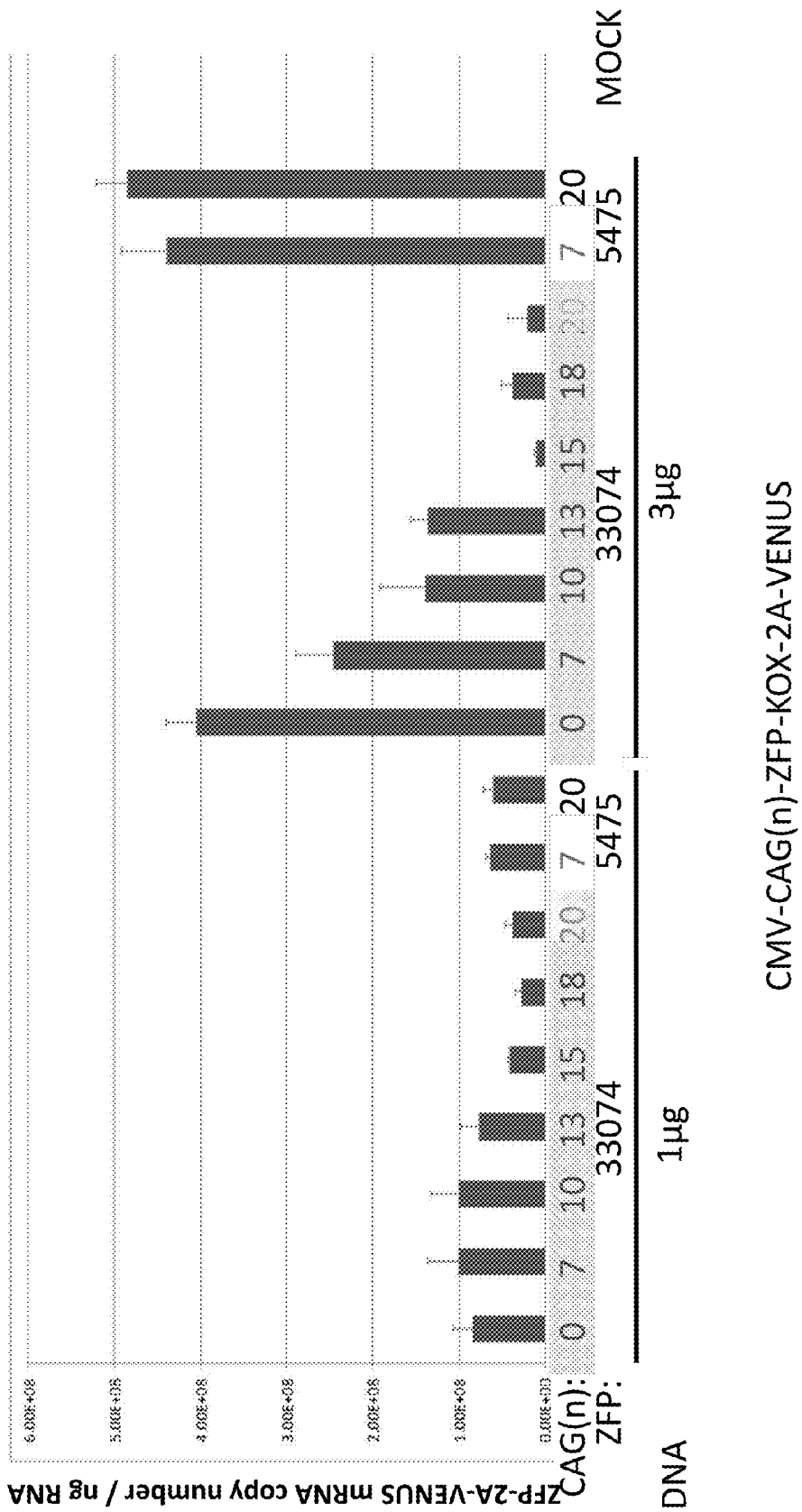
Figure 7:
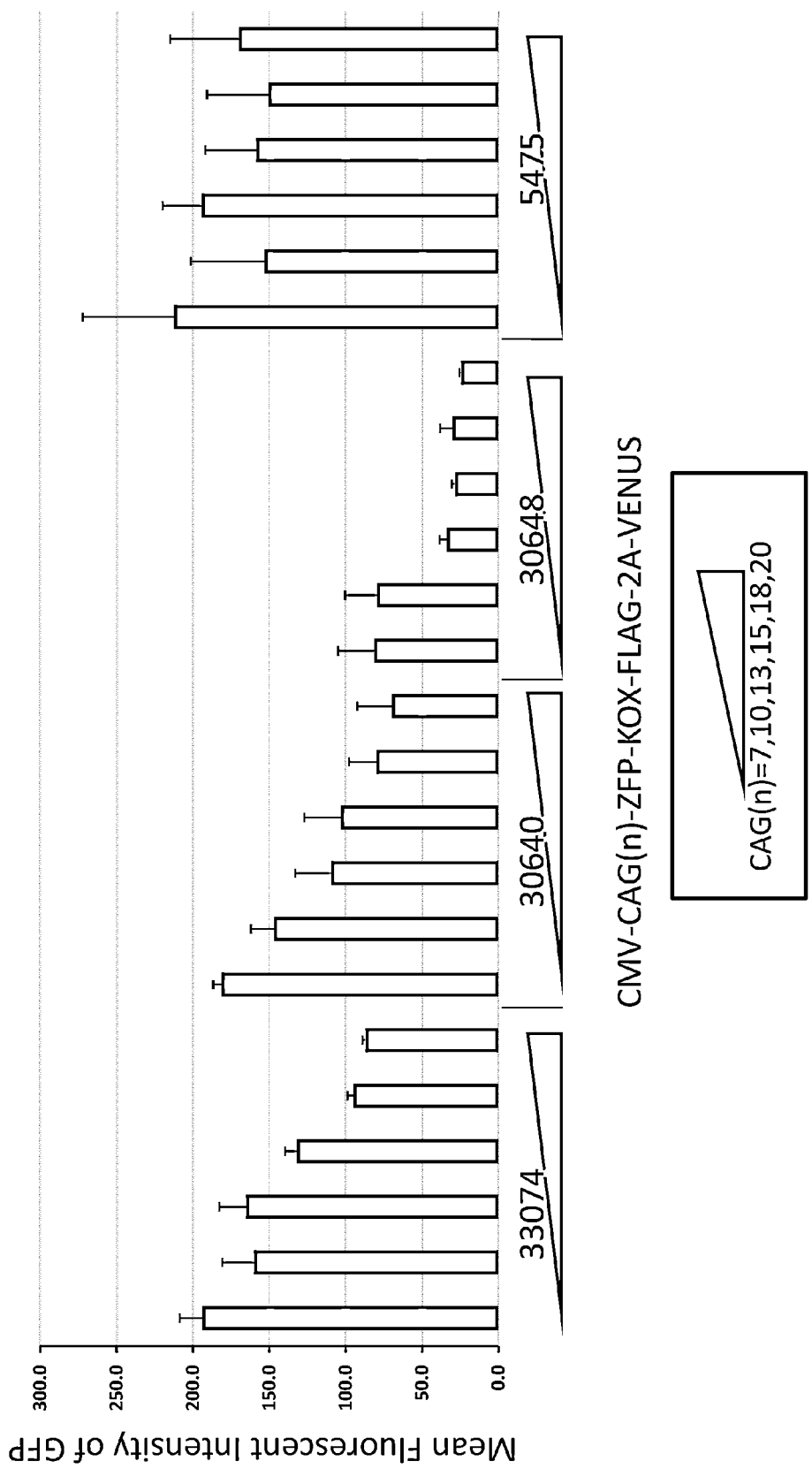
FIG. 7 is a graph depicting analysis of 293T cells transfected with the indicated constructs.

293T cells were transfected with 1 μg (FIGS. 6A and 6B) or 3 μg (FIGS. 6B and 7) of plasmid DNA. The analysis of expression levels of ZFP-2A-VENUS were carried out at 2 days post transfection using flow cytometry (FIG. 6A) and quantitative PCR (Taqman®) analysis (FIG. 6B). In these experiments, 293T cells were transfected with DNA plasmid comprising the CMV-33074-KOX-FLAG-2A-VENUS vector, where the CMV promoter contained a number (between 0 and 20) of CAG repeats (SEQ ID NO: 24); ZFP 33074 binds to CAG repeats.

The results, shown in FIG. 6A, demonstrate that expression of ZFP 33074 is self-regulating using the modified CMV promoter where there are about 15-20 CAG repeats (SEQ ID NO: 20). FIG. 6B shows that when the ZFP expression level was high (e.g. from 3 μg transfection), the ZFP was able to regulate its own expression from a construct that included fewer CAG repeats. The presence of a CAG repeat itself did not reduce the expression of the control ZFP 5475, which does not bind to CAG repeats.

When the modified CMV promoter (with 7-20 CAGs) (SEQ ID NO: 22) was tested with the different CAG binding ZFPs, 33074, 30640 or 30648, the more active repressors (30648) required fewer CAG repeats to exhibit self-regulation than weaker repressors (33074 and 30640). See, FIG. 7.

Figure 8A:
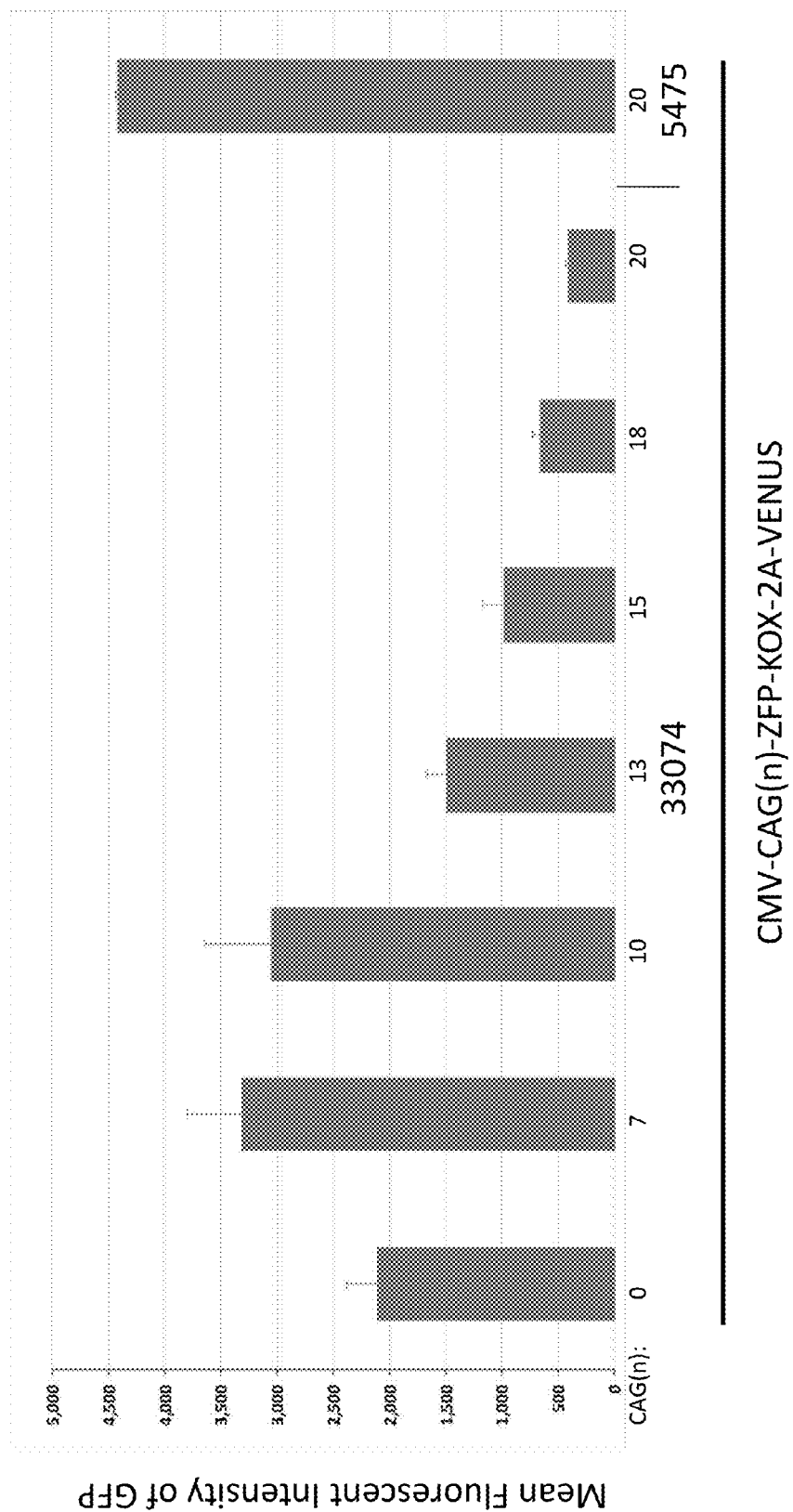
FIGS. 8A to 8C are graphs depicting analysis of 293T cells transduced with AAV comprising the indicated constructs.
Figure 8B:
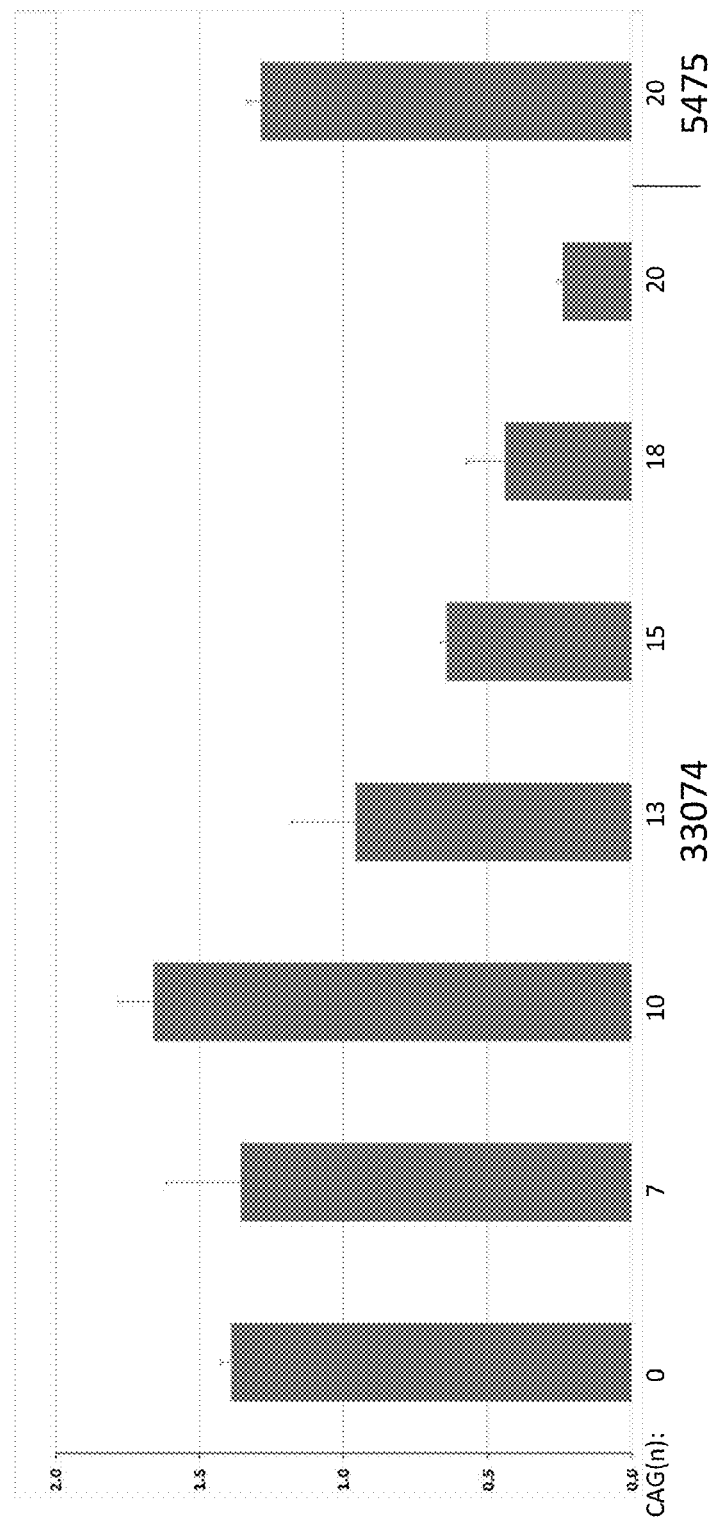
Figure 8C:
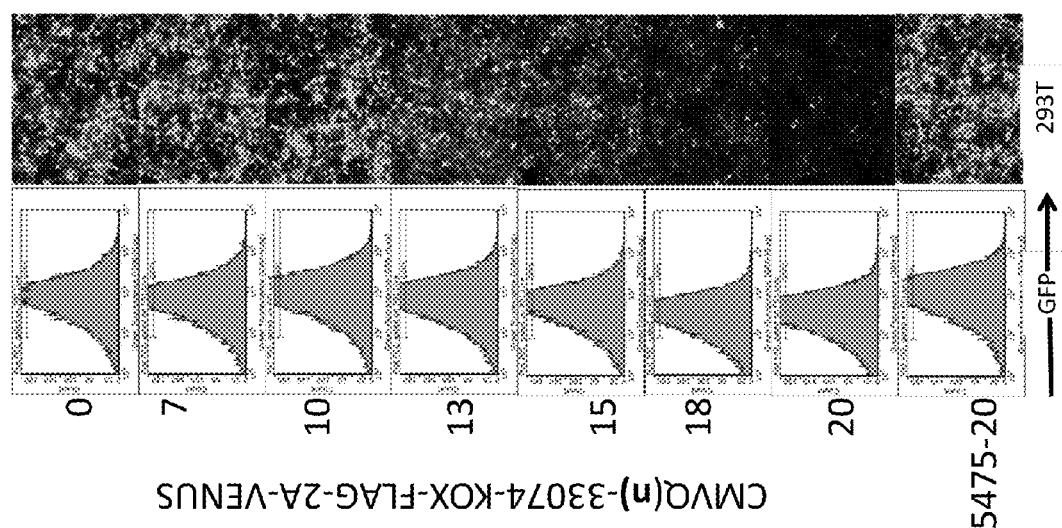

293T cells were also infected with AAV vectors, AAV-CMV-CAG(0-20)-ZFP-2A-VENUS ("CAG(0-20)" disclosed as SEQ ID NO: 24). The 293T cells were harvested 4 days post-transduction and GFP/VENUS expression was measured by flow cytometry (FIG. 8A) or microscopy (FIG. 8C). Quantitative PCR (qPCR) was also performed to determine mRNA levels of ZFP-2A-VENUS (FIG. 8B). Together these results demonstrated that a CAG repeat-targeting ZFP can regulate its own expression levels via target sites (CAG repeat) engineered into the promoter of the expression vector; the longer the CAG repeat region in the promoter is correlated with lower expression of the ZFP.

Figure 9A:
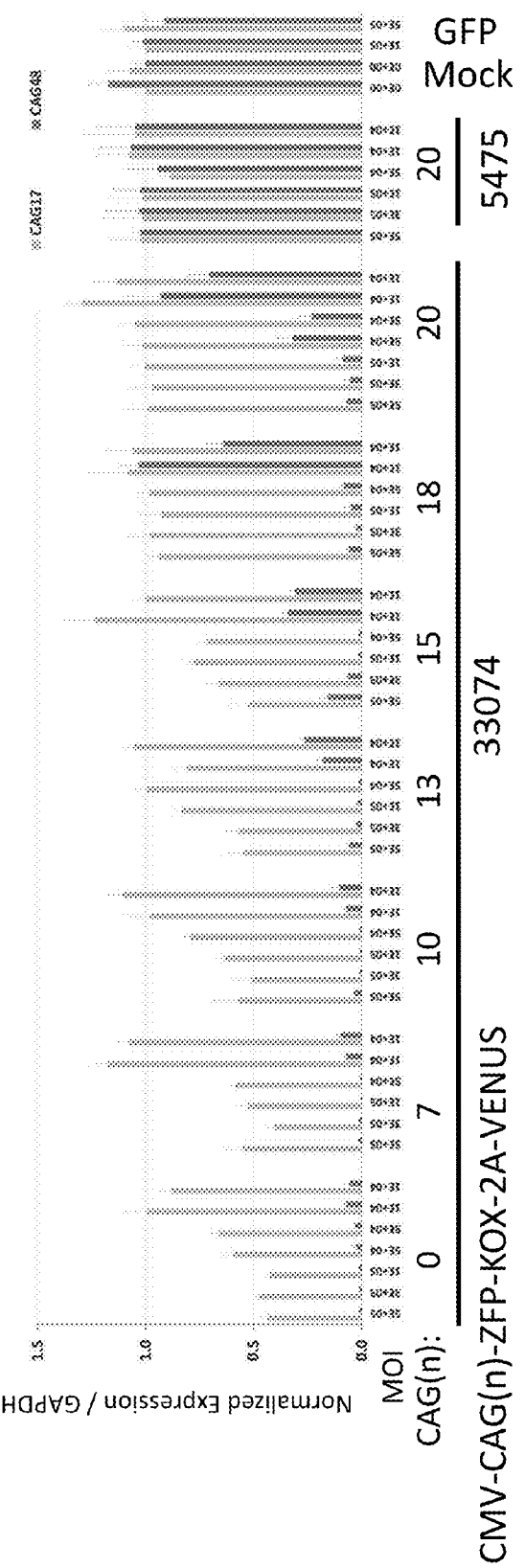
FIGS. 9A and 9B are graphs depicting analysis of HD neurons transduced with different multiplicities of infection (MOI) of AAV containing the promoter constructs as described in Example 1.

The self-regulating promoter constructs comprising ZFP 33074, which is an allele-specific repressor of mutant Htt, were also tested in HD embryonic stem cell-derived neurons carrying a wild type Htt allele ("CAG17" (SEQ ID NO: 23)) and a mutant Htt allele ("CAG48" (SEQ ID NO: 25)). With AAV infection at MOIs higher than 10,000 (see FIG. 9A), ZFP 33074 expressed from the promoter lacking any CAG repeats ("0") was able to partially repress (up to ~50%) the wild type Htt allele (CAG17 (SEQ ID NO: 23)); the mutant Htt allele (CAG48 (SEQ ID NO: 25)) was repressed by ~90% or greater at all doses. In promoter constructs with 18 or 20 CAG repeats (SEQ ID NO: 27), repression of the wild type CAG17 (SEQ ID NO: 23) allele was not observed at any doses. Additionally, in the samples comprising the longer CAG repeat expression constructs, repression of the CAG48 (SEQ ID NO: 25) allele was lower at low MOIs than that from constructs with shorter or no CAG repeats.

Figure 9B:
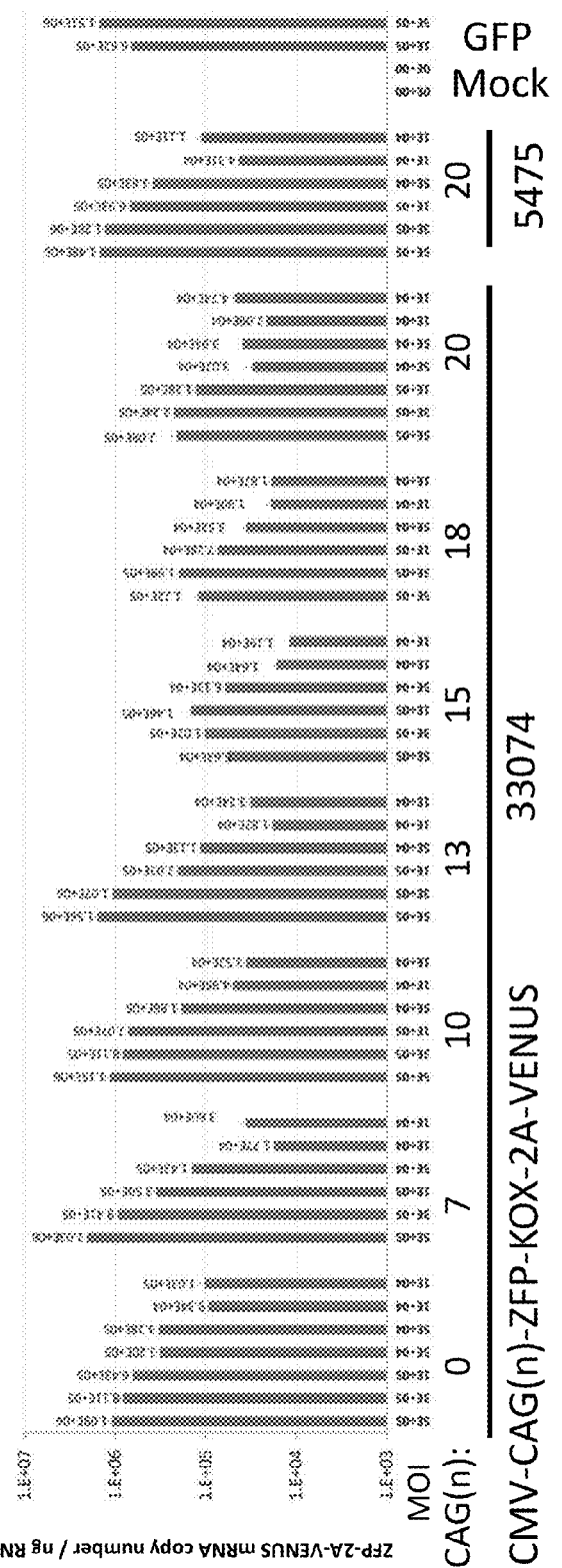

The expression levels of ZFP 33074 were evaluated using a qPCR probe set designed to detect the ZFP 33074 mRNA (FIG. 9B). Longer CAG repeats in the promoter of the expression vectors are in general correlated with reduced expression of the ZFP.

Together, these examples show that ZFPs can regulate expression through target sites engineered into the promoter of the expression construct, and the degree of self-regulation is dependent on the number of binding sites that are included in the expression construct. These results also show that such self-regulation is feasible in the context of a plasmid vector, or an AAV, LV or IDLV vector.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A construct comprising a polynucleotide encoding at least one component of a non-naturally occurring gene modulator that binds to an intended target site, wherein the polynucleotide is operably linked to a heterologous promoter comprising a self-regulating target site bound by the gene modulator and further wherein binding of the gene modulator to the self-regulating target sequence modulates expression of the polynucleotide.

2. The construct of claim 1, wherein the intended target site is in the genome of a cell.

3. The construct of claim 1, wherein expression of the polynucleotide is decreased upon binding of the gene modulator to the self-regulating target sequence.

4. The construct of claim 1, wherein the self-regulating target site differs from the sequence of the intended target site by at least one base pair.

5. The construct of claim 1, wherein the construct comprises a control element and the self-regulating target site is within the control element.

6. The construct of claim 1, wherein the construct is a viral construct.

7. The construct of claim 6, wherein the viral construct is a lentivirus (LV), an integration defective lentiviral vector (IDLV), an adenovirus or an AAV construct.

8. The construct of claim 1, wherein the gene modulator is a transcription factor or a nuclease.

9. The construct of claim 8, wherein the transcription factor or the nuclease comprises a zinc finger protein, a TALE protein or a CRISPR/Cas system.

10. The construct of claim 8, further comprising a donor nucleic acid.

11. The construct of a claim 1, further comprising at least one additional polypeptide-encoding sequence operably linked to the sequence encoding the gene modulator and the self-regulating target site.

12. The construct of claim 11, wherein the at least one additional polypeptide-encoding sequence is separated from the sequence encoding the gene regulator by a 2A self-cleaving peptide sequence or an IRES site.

13. A cell comprising the construct of claim 1.

14. The cell of claim 13, wherein the gene modulator comprises a nuclease and further wherein the cell comprises a donor nucleic acid that is integrated into the genome of the cell.

15. The cell of claim 14, wherein the donor nucleic acid is in an adeno-associated viral vector (AAV) or is encoded by a plasmid DNA.

16. A pharmaceutical composition comprising a construct according to claim 1.

17. A pharmaceutical composition comprising a cell according to claim 13.

18. A kit comprising the construct of claim 1.

19. The kit of claim 17, further comprising a donor molecule and instructions.

20. A method of regulating expression of an exogenous gene modulator introduced into a cell, the method comprising introducing a construct according to claim 1 into a cell, wherein expression of the gene modulator is modulated upon binding of the gene modulator to the self-regulating target site.

21. The method of claim 20, wherein the cell is a mammalian or plant cell.

22. The method of claim 20, wherein the cell is a stem cell.

\* \* \* \* \*

SEQUENCE LISTING

```
<160> NUMBER OF SEQ ID NOS: 28

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Asp Asn Leu Ser Glu
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Arg Cys Asn Leu Arg Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ser Gly Asp Leu Thr Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 4

Gln Ser Ser Asp Leu Ser Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Trp Ser Thr Arg Lys Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Gly His Leu Gln Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Ser Gly Asn Leu Thr Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Arg Ser His Leu Ala Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Asp Val Leu Ser Thr
1               5

<210> SEQ ID NO 10

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Arg Ser Arg Leu Arg Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ser Asp Asp Leu Ser Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Asn Asp Asn Arg Thr Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Asp Asp Leu Thr Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Asp Asp Arg Lys Thr
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

-continued

Gln Ser Ser Asp Leu Arg Arg
1               5

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agcagcagca gcagcagcag cagcagca                                       28

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cagcagcagc agcagcagca gcagcagc                                       28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccgggacggg tccaagatgg acggccgc                                       28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acgctgcgcc ggcggaggcg gggccgcg                                       28

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(60)
<223> OTHER INFORMATION: This sequence may encompass 15-20 'cag' repeats

<400> SEQUENCE: 20
cagcagcagc agcagcagca gcagcagcag cagcagcagc agcagcagca gcagcagcag    60

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic

```
            oligonucleotide
<220> FEATURE:
<221> NAME/KEY: misc_feature
<222> LOCATION: (1)..(21)
<223> OTHER INFORMATION: This sequence may encompass 6-7 'cag' repeats

<400> SEQUENCE: 21
cagcagcagc agcagcagca g                                             21

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(60)
<223> OTHER INFORMATION: This sequence may encompass 7-20 'cag' repeats

<400> SEQUENCE: 22
cagcagcagc agcagcagca gcagcagcag cagcagcagc agcagcagca gcagcagcag    60

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cagcagcagc agcagcagca gcagcagcag cagcagcagc agcagcagca g             51

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(60)
<223> OTHER INFORMATION: This sequence may encompass 0-20 'cag' repeats

<400> SEQUENCE: 24
cagcagcagc agcagcagca gcagcagcag cagcagcagc agcagcagca gcagcagcag    60

<210> SEQ ID NO 25
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcag                                         144

<210> SEQ ID NO 26
<211> LENGTH: 9
<212> TYPE: PRT
<213> ORGANISM: Unknown
```

```
<220> FEATURE:
<223> OTHER INFORMATION: Description of Unknown: 'LAGLIDADG'
      family peptide

<400> SEQUENCE: 26

Leu Ala Gly Leu Ile Asp Ala Asp Gly
1               5

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(60)
<223> OTHER INFORMATION: This sequence may encompass 18 or 20 'cag'
      repeats

<400> SEQUENCE: 27
cagcagcagc agcagcagca gcagcagcag cagcagcagc agcagcagca gcagcagcag      60

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(60)
<223> OTHER INFORMATION: This sequence may encompass 7, 10, 13, 15, 18
      or 20 'cag' repeats

<400> SEQUENCE: 28
cagcagcagc agcagcagca gcagcagcag cagcagcagc agcagcagca gcagcagcag      60
```